(12) United States Patent
Grass

(10) Patent No.: US 7,998,687 B2
(45) Date of Patent: Aug. 16, 2011

(54) BIOMARKERS FOR CHRONIC TRANSPLANT DYSFUNCTION

(75) Inventor: Peter Grass, Schopfheim (DE)

(73) Assignees: Novartis AG, Basel (CH); Novartis Pharma GmbH, Vienna (AT)

( * ) Notice: Subject to any disclaimer, the term of this patent is extended or adjusted under 35 U.S.C. 154(b) by 280 days.

(21) Appl. No.: 12/297,258

(22) PCT Filed: Apr. 19, 2007

(86) PCT No.: PCT/EP2007/003437
§ 371 (c)(1),
(2), (4) Date: Oct. 15, 2008

(87) PCT Pub. No.: WO2007/121922
PCT Pub. Date: Nov. 1, 2007

(65) Prior Publication Data
US 2009/0304705 A1 Dec. 10, 2009

(30) Foreign Application Priority Data
Apr. 21, 2006 (GB) .................................. 0607943.8

(51) Int. Cl.
*G01N 33/53* (2006.01)

(52) U.S. Cl. .......................... 435/7.1; 435/7.2; 436/518
(58) Field of Classification Search ....................... None
See application file for complete search history.

(56) References Cited

U.S. PATENT DOCUMENTS
2003/0104371 A1    6/2003    Strom et al. ...................... 435/6

FOREIGN PATENT DOCUMENTS

| WO | 99/15700 | 4/1999 |
|---|---|---|
| WO | 03/062467 | 7/2003 |
| WO | 2004/018710 | 3/2004 |
| WO | 2004/074815 | 9/2004 |

OTHER PUBLICATIONS

Racusen L.C. et al., "The banff 97 working classification of renal allograft pathology", Kidney International, vol. 55, pp. 713-723, (1999).
Nankivell B.J. et al., "The natural history of chronic allograft nephropathy", The New England Journal of Medicine, vol. 349, No. 24, pp. 2326-2333, (2003).

*Primary Examiner* — Jacob Cheu
(74) *Attorney, Agent, or Firm* — Leslie Fischer

(57) ABSTRACT

The invention relates to the analysis and identification of genes that are modulated in transplant rejection. This alteration of gene expression provides a molecular signature to accurately detect transplant rejection.

14 Claims, 2 Drawing Sheets

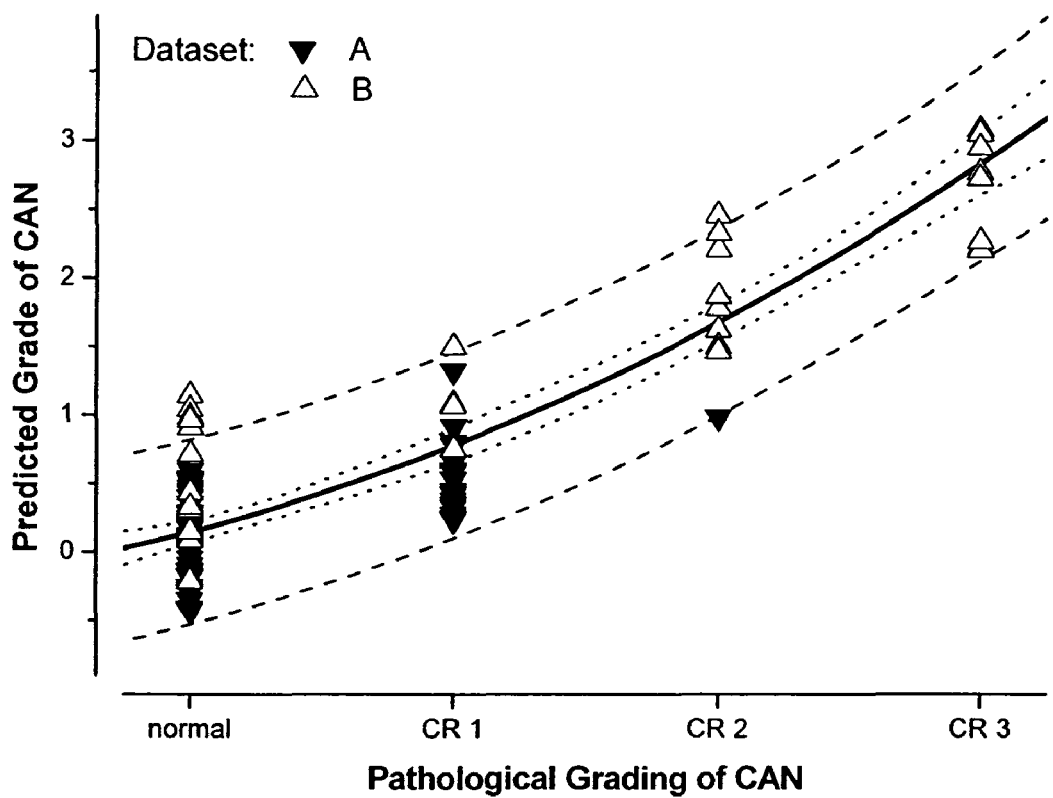
Figure 1: Model predicted versus actual grades of chronic rejection.

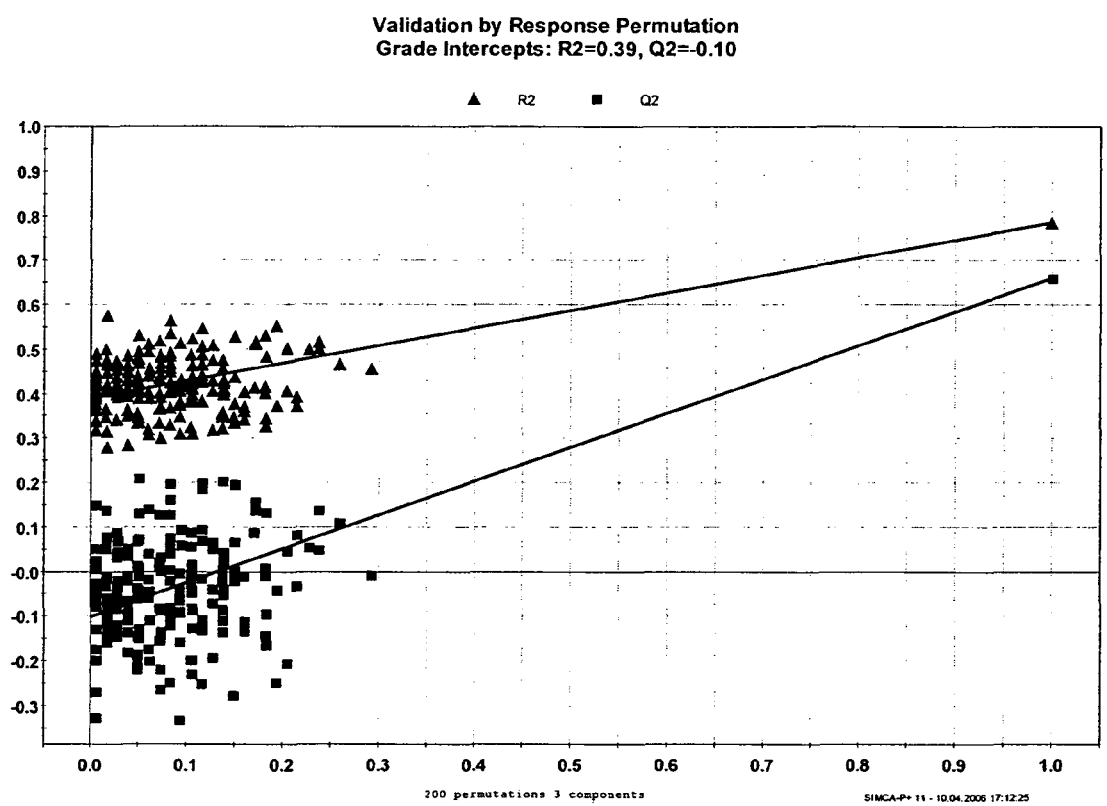
Figure 2: Validation by response permutation.

BIOMARKERS FOR CHRONIC TRANSPLANT DYSFUNCTION

This application is a 371 of PCT/EP2007/003437 filed on Apr. 19, 2007, which claims benefit of Great Britain Application No. 0607943.8 filed on Apr. 21, 2006, which in their entirety are herein incorporated by reference.

FIELD OF THE INVENTION

This invention relates generally to the analytical testing of tissue samples in vitro, and more particularly to gene- or protein-based tests useful in clinical diagnosis of chronic transplant dysfunction, e.g., chronic allograft nephropathy.

BACKGROUND OF THE INVENTION

Chronic transplant dysfunction is a phenomenon in solid organ transplants displaying a gradual deterioration of graft function months to years after transplantation, eventually leading to graft failure, and which is accompanied by characteristic histological features. Clinically, chronic transplant dysfunction in kidney grafts, e.g., chronic/sclerosing allograft nephropathy ("CAN"), manifests itself as a slowly progressive decline in glomerular filtration rate, usually in conjunction with proteinuria and arterial hypertension. Despite clinical application of potent immunoregulatory drugs and biologic agents, chronic rejection remains a common and serious post-transplantation complication. Chronic rejection is a relentlessly progressive process.

The single most common cause for early graft failure, especially within one month post-transplantation, is immunologic rejection of the allograft. The unfavorable impact of the rejection is magnified by the fact that: (a) the use of high-dose anti-rejection therapy, superimposed upon maintenance immunosuppression, is primarily responsible for the morbidity and mortality associated with transplantation, (b) the immunization against "public" HLA-specificities resulting from a rejected graft renders this patient population difficult to retransplant and (c) the return of the immunized recipient with a failed graft to the pool of patients awaiting transplantation enhances the perennial problem of organ shortage.

Histopathological evaluation of biopsy tissue is the gold standard for the diagnosis of CAN, while prediction of the onset of CAN is currently impossible. Current monitoring and diagnostic modalities are ill-suited to the diagnosis of CAN at an early stage. Accordingly, a need exists for identifying molecular tests that are more sensitive and which can be used in clinical diagnosis of rejection, especially in its early and/or pre-clinical state.

SUMMARY

The invention pertains to molecular diagnostic methods using gene expression profiling to further refine the BANFF 97 disease classification (Racusen L C, et al., Kidney Int. 55(2):713-23 (1999)). The invention also provides methods for using biomarkers as predictive or early diagnostic biomarkers when applied at early time points after transplantation when graft dysfunction by other more conventional means is not yet detectable.

Accordingly, the invention pertains to a method for assessing the onset of a rejection of a transplanted organ in a subject, comprising the steps of (a) obtaining a post-transplantation sample from the subject; (b) determining the level of gene expression in the post-transplantation sample of a combination of a plurality of genes selected from the group consisting of the genes identified in Table 2; (c) comparing the magnitude of gene expression of the at least one gene in the post-transplantation sample with the magnitude of gene expression of the same gene in a control sample; and (d) determining whether the expression level of at least one gene is up-regulated or down-regulated relative to the control sample, wherein up-regulation or down-regulation of at least one gene indicates that the subject is likely to experience transplant rejection, thereby assessing the onset of rejection of the transplanted organ in the subject.

An another aspect, the invention pertains to a method for assessing the onset of a rejection of a transplanted organ in a subject, comprising the steps of: (a) obtaining a post-transplantation sample from the subject; (b) determining the level of gene expression in the post-transplantation sample of a combination of a plurality of genes selected from the group consisting of the genes identified in Table 2; and (c) comparing the gene expression pattern of the combination of gene in the post-transplantation sample with the pattern of gene expression of the same combination of gene in a control sample, wherein a similarity in the expression pattern of the gene expression pattern of the combination of gene in the post-transplantation sample compared to the expression pattern of the same combination of gene in a control sample expression profile indicates that the subject is likely to experience transplant rejection, thereby assessing the onset of rejection of the transplanted organ in the subject.

In another aspect, the invention pertains to a method for assessing the progression of rejection of a transplanted organ in a subject, comprising the steps of: (a) obtaining a post-transplantation sample from the subject; (b) determining the level of gene expression in the post-transplantation sample of a combination of a plurality of genes selected from the group consisting of the genes identified in Table 2; and (c) comparing the gene expression pattern of the combination of gene in the post-transplantation sample with the pattern of gene expression of the same combination of gene in a control sample, wherein a similarity in the expression pattern of the gene expression pattern of the combination of gene in the post-transplantation sample compared to the expression pattern same combination of gene in a control sample expression profile indicates a grade of transplant rejection, thereby assessing the progression of rejection of the transplanted organ in the subject. The stage of transplant rejection can be selected from the group consisting of: grade I; grade II; and grade III.

In another aspect, the invention pertains to a method of monitoring transplant rejection in a subject, comprising the steps of: (a) taking as a baseline value the magnitude of gene expression of a combination of a plurality of genes in a sample obtained from a transplanted subject who is known not to develop rejection; (b) detecting a magnitude of gene expression corresponding to the combination of a plurality of genes in a sample obtained from a patient post-transplantation; and (c) comparing the first value with the second value, wherein a first value lower or higher than the second value predicts that the transplanted subject is at risk of developing rejection, wherein the plurality of genes are selected from the group of genes identified in Table 2.

In another aspect, the invention pertains to a method of monitoring transplant rejection in a subject, comprising the steps of: (a) detecting a pattern of gene expression corresponding to a combination of a plurality of genes from a sample obtained from a donor subject at the day of transplantation; (b) detecting a pattern of gene expression corresponding to the plurality of genes from a sample obtained from a recipient subject post-transplantation; and (c) comparing the first value with the second value, wherein a first value lower or higher than the second value predicts that the recipient subject is at risk of developing rejection; wherein a plurality of genes are selected from the group consisting of the genes identified in Table 2.

In another aspect, the invention pertains to a method for monitoring transplant rejection in a subject at risk thereof, comprising the steps of: (a) obtaining a pre-administration sample from a transplanted subject prior to administration of a rejection inhibiting agent; (b) detecting the pattern of gene expression of a plurality of genes in the pre-administration sample; (c) obtaining one or more post-administration samples from the transplanted subject; (d) detecting the pattern of gene expression of a plurality of genes in the post-administration sample or samples; (e) comparing the pattern of gene expression of the plurality of genes in the pre-administration sample with the pattern of gene expression in the post-administration sample or samples; and (f) adjusting the agent accordingly, wherein the plurality of genes are selected from the group consisting of the genes of the genes identified in Table 2.

In another aspect, the invention pertains to a method for preventing, inhibiting, reducing or treating transplant rejection in a subject in need of such treatment comprising administering to the subject a compound that modulates the synthesis, expression or activity of one or more genes or gene products encoded thereof of genes selected from the group consisting of the genes of the genes identified in Table 2, so that at least one symptom of rejection is ameliorated.

In another aspect, the invention pertains to a method for identifying agents for use in the prevention, inhibition, reduction or treatment of transplant rejection comprising monitoring the level of gene expression of one or more genes or gene products selected from the group consisting of the genes identified in Table 2.

The transplanted subject is a kidney transplanted subject. The pattern of gene expression can be assessed by detecting the presence of a protein encoded by the gene. The presence of the protein can be detected using a reagent which specifically binds to the protein. The pattern of gene expression can be detected by techniques selected from the group consisting of Northern blot analysis, reverse transcription PCR and real time quantitative PCR. The magnitude of gene expression of one gene or a plurality of a combination of genes can be detected by reverse transcription PCR or microarrays.

In another aspect, the invention pertains to the use of the combination of the plurality of genes or an expression products thereof as listed in Table 2 as a biomarker for transplant rejection.

In another aspect, the invention pertains to the use of a compound which modulates the synthesis, expression of activity of one or more genes as identified in Table 2, or an expression product thereof, for the preparation of a medicament for prevention or treatment of transplant rejection in a subject.

In another aspect, the invention pertains to a method or use according to any preceding claim, wherein the transplant rejection is chronic/sclerosing allograft nephropathy and the gene is selected from the group consisting of the genes identified in Table 2.

BRIEF DESCRIPTION OF DRAWINGS

FIG. 1 is a graph derived by PLS of data comparing observed versus predicted grade of chronic rejection;

FIG. 2 is a graph of showing the predictive performance of biomarker derived by PLS using Response Permutation.

DETAILED DESCRIPTION

Definitions

To further facilitate an understanding of the present invention, a number of terms and phrases are defined below:

The terms "down-regulation" or "down-regulated" are used interchangeably herein and refer to the decrease in the amount of a target gene or a target protein. The term "down-regulation" or "down-regulated" also refers to the decreases in processes or signal transduction cascades involving a target gene or a target protein.

The term "transplantation" as used herein refers to the process of taking a cell, tissue, or organ, called a "transplant" or "graft" from one subject and placing it or them into a (usually) different subject. The subject who provides the transplant is called the "donor" and the subject who received the transplant is called the "recipient". An organ, or graft, transplanted between two genetically different subjects of the same species is called an "allograft". A graft transplanted between subjects of different species is called a "xenograft".

The term "transplant rejection" as used herein is defined as functional and structural deterioration of the organ due to an active immune response expressed by the recipient, and independent of non-immunologic causes of organ dysfunction.

The term "chronic allograft nephropathy" "CAN" as used herein refers to late renal allograft loss, other than that associated with the death of the patient. It represents an incremental damage to the nephrons from time-dependent immunologic and nonimmunologic causes. It is characterized by progressive renal dysfunction accompanied by chronic interstitial fibrosis, tubular atrophy, vascular occlusive changes, and glomerulosclerosis.

The term "chronic rejection" as used herein refers to a rejection of the transplanted organ (e.g., kidney) developing after the first 30-120 post-transplant days. In kidneys, the development of nephrosclerosis (hardening of the renal vessels), with proliferation of the vascular intima of renal vessels, and intimal fibrosis, with marked decrease in the lumen of the vessels, takes place. The result is renal ischemia, hypertension, tubular atrophy, interstitial fibrosis, and glomerular atrophy with eventual renal failure. In addition to the established influence of HLA incompatibility, the age, number of nephrons, and ischemic history of a donor kidney may contribute to ultimate progressive renal failure in transplanted patients.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

A "gene" includes a polynucleotide containing at least one open reading frame that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art, some of which are described herein.

A "gene product" includes an amino acid (e.g., peptide or polypeptide) generated when a gene is transcribed and translated.

The term "magnitude of gene expression" as used herein refers to quantifying marker gene transcripts and comparing this quantity to the quantity of transcripts of a constitutively expressed gene. The term "magnitude of gene expression" means a "normalized, or standardized amount of gene expression". For example, the overall expression of all genes in cells varies (i.e., it is not constant). To accurately assess whether the detection of increased mRNA transcript is significant, it is preferable to "normalize" gene expression to accurately compare levels of expression between samples, i.e., it is a baselevel against which gene expression is compared. Quantification of gene transcripts was accomplished using microarray analysis and the magnitude of gene expression was calculated relative to samples with normal kidney function, i.e., the relative deviation from normal was measured.

The term "differentially expressed", as applied to a gene, includes the differential production of mRNA transcribed from a gene or a protein product encoded by the gene. A differentially expressed gene may be overexpressed or underexpressed as compared to the expression level of a normal or control cell. In one aspect, it includes a differential that is at least 1.1 times, 1.2 times, 1.3 times, 1.4 times, 1.5 times, 1.6 times, 1.7 times, 1.8 times, 1.9 times, 2 times, at least 3 times, at least 4 times, at least 5 times, at least 6 times, at least 7 times, at least 8 times, at least 9 times or at least 10 times higher or lower than the expression level detected in a control sample. In a preferred embodiment, the expression is higher than the control sample. The term "differentially expressed" also includes nucleotide sequences in a cell or tissue which are expressed where silent in a control cell or not expressed where expressed in a control cell. In particular, this term refers to refers to a given allograft gene expression level and is defined as an amount which is substantially greater or less than the amount of the corresponding baseline expression level. Baseline is defined here as being the level of expression in healthy tissue. Healthy tissue includes a transplanted organ without pathological findings.

The term "sample" as used herein refers to cells obtained from a biopsy. The term "sample" also refers to cells obtained from a fluid sample including, but not limited to, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft. A fluid test sample may also be obtained from essentially any body fluid including: blood (including peripheral blood), lymphatic fluid, sweat, peritoneal fluid, pleural fluid, bronchoalveolar lavage fluid, pericardial fluid, gastrointestinal juice, bile, urine, feces, tissue fluid or swelling fluid, joint fluid, cerebrospinal fluid, or any other named or unnamed fluid gathered from the anatomic area in proximity to the allograft or gathered from a fluid conduit in fluid communication with the allograft. A "post-transplantation fluid test sample" refers to a sample obtained from a subject after the transplantation has been performed.

Sequential samples can also be obtained from the subject and the quantification of immune activation gene biomarkers determined as described herein, and the course of rejection can be followed over a period of time. In this case, for example, the baseline magnitude of gene expression of the biomarker gene(s) is the magnitude of gene expression in a post-transplant sample taken after the transplant. For example, an initial sample or samples can be taken within the nonrejection period, for example, within one week of transplantation and the magnitude of expression of biomarker genes in these samples can be compared with the magnitude of expression of the genes in samples taken after one week. In one embodiment, the samples are taken 2 weeks, 4 weeks, 8 weeks, 12 weeks, 24 weeks, and 36 weeks post-transplantation, or any combination thereof.

The term "biopsy" as used herein refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. In one embodiment, a fine needle aspiration biopsy is used. In another embodiment, a minicore needle biopsy is used. A conventional percutaneous core needle biopsy can also be used.

The term "up-regulation" or "up-regulated" are used interchangeably herein and refer to the increase or elevation in the amount of a target gene or a target protein. The term "up-regulation" or "up-regulated" also refers to the increase or elevation of processes or signal transduction cascades involving a target gene or a target protein.

The term "gene cluster" or "cluster" as used herein refers to a group of genes related by expression pattern. In other words, a cluster of genes is a group of genes with similar regulation across different conditions, such as graft non-rejection versus graft rejection. The expression profile for each gene in a cluster should be correlated with the expression profile of at least one other gene in that cluster. Correlation may be evaluated using a variety of statistical methods. Often, but not always, members of a gene cluster have similar biological functions in addition to similar gene expression patterns.

A "probe set" as used herein refers to a group of nucleic acids that may be used to detect two or more genes. Detection may be, for example, through amplification as in PCR and RT-PCR, or through hybridization, as on a microarray, or through selective destruction and protection, as in assays based on the selective enzymatic degradation of single or double stranded nucleic acids. Probes in a probe set may be labeled with one or more fluorescent, radioactive or other detectable moieties (including enzymes). Probes may be any size so long as the probe is sufficiently large to selectively detect the desired gene. A probe set may be in solution, as would be typical for multiplex PCR, or a probe set may be adhered to a solid surface, as in an array or microarray. It is well known that compounds such as PNAs may be used instead of nucleic acids to hybridize to genes. In addition, probes may contain rare or unnatural nucleic acids such as inosine.

The terms "polynucleotide" and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for guanine when the polynucleotide is RNA. This, the term "polynucleotide sequence" is the alphabetical representation of a polynucleotide molecule. This alphabetical representation can be inputted into databases in a computer having a central processing unit and used for bioinformatics applications such as functional genomics and homology searching.

The term "cDNAs" includes complementary DNA, that is mRNA molecules present in a cell or organism made into cDNA with an enzyme such as reverse transcriptase. A "cDNA library" includes a collection of mRNA molecules present in a cell or organism, converted into cDNA molecules with the enzyme reverse transcriptase, then inserted into "vectors" (other DNA molecules that can continue to replicate after addition of foreign DNA). Exemplary vectors for libraries include bacteriophage, viruses that infect bacteria (e.g., lambda phage). The library can then be probed for the specific cDNA (and thus mRNA) of interest.

A "primer" includes a short polynucleotide, generally with a free 3'-OH group that binds to a target or "template" present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are well known in the art, and are taught, for example, in MacPherson et al., IRL Press at Oxford University Press (1991)). All processes of producing replicate copies of a polynucleotide, such as PCR or gene cloning, are collectively referred to herein as "replication". A primer can also be used as a probe in hybridization reactions, such as Southern or Northern blot analyses (see, e.g., Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

The term "polypeptide" includes a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

The term "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to hydrogen bond with each other, according to generally accepted base-pairing rules.

As used herein, the terms "marker" and "biomarker" are used interchangeably and include a polynucleotide or polypeptide molecule which is present or modulated (i.e., increased or decreased) in quantity or activity in subjects at risk for organ rejection relative to the quantity or activity in subjects that are not at risk for organ rejection. The relative change in quantity or activity of the biomarker is correlated with the incidence or risk of incidence of rejection.

As used herein, the term "panel of markers" includes a group of biomarkers, the quantity or activity of each member of which is correlated with the incidence or risk of incidence of organ rejection. In certain embodiments, a panel of biomarkers may include only those biomarkers which are either increased in quantity or activity in subjects at risk for organ rejection. In other embodiments, a panel of biomarkers may include only those biomarkers which are either decreased in quantity or activity in subjects at risk for organ rejection.

Abbreviations for select terms are summarized in Table 1 below.

TABLE 1

Abbreviations

| Abbreviation | Term |
| --- | --- |
| BMD | BioMarker Development |
| CAN | Chronic allograft nephropathy |
| CR 1, CR 2, CR 3 | Banff classification of chronic allograft nephropathy of grade 1 to 2 |
| PLS | Projections of latent structures by means of partial least squares |

Transplant Rejection

The present invention relates to the identification of genes, which are differentially regulated during rejection, in particular during chronic rejection. A highly statistically significant correlation has been found between the expression of a combination of gene and chronic rejection, thereby providing a "molecular signature" for transplant rejection (e.g., chronic renal rejection). By virtue of the co-expression of these genes organs that are likely to undergo rejection, these genes and their expression products can be used in the management, prognosis and treatment of patients at risk of transplant rejection.

Accordingly, in one aspect the invention pertains to using a recognition signature comprising a combination of genes shown in Table 2 to indicate transplant rejection, in particular chronic rejection of a transplanted organ.

Chronic rejection is probably caused by multiple factors: antibodies as well as lymphocytes. The definitive diagnosis of chronic rejection is generally made by biopsy of the organ in question. Kidneys with chronic rejection have fibrosis (scarring) and damage to the microscopic blood vessels in the substance of the kidney.

The differentiation of the diagnosis of rejection from other etiologies for graft dysfunction and institution of effective therapy is complicated because: (a) the percutaneous core needle biopsy of grafts, the best of available current tools to diagnose rejection is performed usually after the "fact", i.e., graft dysfunction and graft damage (irreversible in some instances) are already present, (b) the morphological analysis of the graft provides modest clues with respect to the potential for reversal of a given rejection episode, and minimal clues regarding the likelihood of recurrence ("rebound"), and (c) the mechanistic basis of the rejection phenomenon, a prerequisite for the design of therapeutic strategies, is poorly defined by current diagnostic indices, including morphologic features of rejection.

The diagnosis of, for example, renal allograft rejection is made usually by the development of graft dysfunction (e.g., an increase in the concentration of serum creatinine) and morphologic evidence of graft injury in areas of the graft also manifesting mononuclear cell infiltration. Two caveats apply, however, to the use of abnormal renal function as an indicator of the rejection process: first, deterioration in renal function is not always available as a clinical clue to diagnose rejection since many of the cadaveric renal grafts suffer from acute (reversible) renal failure in the immediate post-transplantation period due to injury from harvesting and ex-vivo preservation procedures. Second, even when immediately unimpaired renal function is present, graft dysfunction might develop due to a non-immunologic cause, such as immunosuppressive therapy itself.

For example, cyclosporine (CsA) nephrotoxicity, a complication that is not readily identified solely on the basis of plasma/blood concentrations of CsA, is a common complication. The clinical importance of distinguishing rejection from CsA nephrotoxicity cannot be overemphasized since the therapeutic strategies are diametrically opposite: escalation of immunosuppressants for rejection, and reduction of CsA dosage for nephrotoxicity.

The invention is based, in part, on the observation that increased or decreased expression of many different genes and/or the encoded proteins is associated with certain graft rejection states. As a result of the data described herein, methods are now available for the rapid and reliable diagnosis of chronic rejection, even in cases where allograft biopsies show only mild cellular infiltrates. Described herein for the first time is an analysis of genes that are differentially regulated simultaneously and which provide a molecular signature to accurately detect transplant rejection.

In addition, the invention is partly based on the observation that genes are expressed as gene clusters—groups of genes, often functionally related, that have substantially related expression profiles under certain circumstances. Accordingly, the invention provides clusters of genes, the expression of the members of which is correlated with graft rejection. The invention further provides classic molecular methods and large scale methods for measuring expression of suitable marker genes.

The methods described herein are particularly useful for detecting chronic transplant rejection. Most typically, the subject (i.e., the recipient of a transplant) is a mammal, such as a human. The transplanted organ can include any transplantable organ or tissue, for example kidney, heart, lung, liver, pancreas, bone, bone marrow, bowel, nerve, stem cells (or stem cell-derived cells), tissue component and tissue composite. In a preferred embodiment, the transplant is a kidney transplant.

The methods described herein are useful to assess the efficacy of anti-rejection therapy. Such methods involve comparing the pre-administration magnitude of the transcripts of the marker genes to the post-administration magnitude of the transcripts of the same genes, where a post-administration magnitude of the transcripts of the genes that is less than the pre-administration magnitude of the transcripts of the same genes indicates the efficacy of the anti-rejection therapy. Any candidates for prevention and/or treatment of transplant rejection, (such as drugs, antibodies, or other forms of rejection or prevention) can be screened by comparison of magnitude of marker expression before and after exposure to the candidate. In addition, valuable information can be gathered in this manner to aid in the determination of future clinical management of the subject upon whose biological material the assessment is being performed. The assessment can be performed using a sample from the subject, using the methods described herein for determining the magnitude of gene expression of the marker genes. Analysis can further comprise detection of an infectious agent.

Biomarkers of Chronic Rejection

The invention is based, in part, on the discovery that selected genes are modulated in chronic transplant dysfunction, e.g., CAN. Chronic rejection (CR) is an indolent, but progressive form of allograft injury that is usually irreversible and eventually results in the failure of most vascularized solid organ allografts. It is the single most significant obstacle to morbidity-free long-term survival. By 5 years after transplantation, it affects as many as 30-50% of heart, lung, pancreas and kidney allograft recipients.

Advances in highly parallel, automated DNA hybridization techniques combined with the growing wealth of human gene sequence information have made it feasible to simultaneously analyze expression levels for thousands of genes (see, e.g., Schena et al., 1995, Science 270:467-470; Lockhart et al., 1996, Nature Biotechnology 14:1675-1680; Blanchard et al., 1996, Nature Biotechnology 14:1649; Ashby et al., U.S. Pat. No. 5,569,588, issued Oct. 29, 1996; Perou et al., 2000, Nature 406:747-752). Methods such as the gene-by-gene quantitative RT-PCR are highly accurate but relatively labor intensive. While it is possible to analyze the expression of thousands of genes using quantitative PCR, the effort and expense would be enormous. Instead, as an example of large scale analysis, an entire population of mRNAs may be converted to cDNA and hybridized to an ordered array of probes that represent anywhere from ten to ten thousand or more genes. The relative amount of cDNA that hybridizes to each of these probes is a measure of the expression level of the corresponding gene. The data may then be statistically analyzed to reveal informative patterns of gene expression. Indeed, early diagnosis of renal allograft rejection and new prognostic biomarkers are important to minimize and personalize immunosuppression. In addition to histopathological differential diagnosis, gene expression profiling significantly improves disease classification by defining a "molecular signature."

Several previous studies have successfully applied a transcriptomic approach to distinguish different classes of kidney transplants. However, the heterogeneity of microarray platforms and various data analysis methods complicates the identification of robust signatures of CAN.

To address this issue, supervised learning algorithms (e.g., PLS) were applied to the gene expression profiles of renal protocol biopsies from patients with stable graft function and patients who had diagnosed with varying grades of CAN. As presented in Example I, this study identified the intersection of multiple gene expression signatures from different microarray datasets to derive descriptors (i.e., gene markers; biomarkers) useful in models, e.g., PLS model, which can accurately predict tissue with different grades of CAN. That is, the present invention relates to the identification of genes, which are modulated (i.e., up-regulated or down-regulated) during rejection, in particular during CAN progression. A highly statistically significant correlation has been found between the expression of one or more biomarker gene(s) and CAN, thereby providing a "molecular signature" for transplant rejection (e.g., CAN). These biomarker genes and their expression products can be used in the management, prognosis and treatment of patients at risk of transplant rejection as they are useful to identify organs that are likely to undergo rejection and/or to determine the grade of disease (e.g., CAN) progression.

The data disclosed herein demonstrate that in actual clinical situations, and in the absence of molecular manipulations of gene expression, combinations of genes are indicative of CAN. In one embodiment, the combination of biomarker genes that form a molecular signature after tissue transplantation are those shown in Table 2. The first column of Table 2 shows the Affymetrix Probeset ID and the second column presents the UNIGENE ID of the related gene. Column 3 and 4 display the gene symbol and the gene name. Column 5 shows the raw expression intensities of the gene averaged over all normal renal functions, and columns 6-9 show the normalized values under normal, CR 1, CR 2, and CR 3 conditions. The genes are listed in an alphabetical order, not according to their predictive power.

TABLE 2

Biomarker Genes of the Invention

| Affymetrix Probeset ID | UNIGENE | Symbol | Gene Name | Raw | Normalized Values | | | |
|---|---|---|---|---|---|---|---|---|
| | | | | | normal | CR 1 | CR 2 | CR 3 |
| 230602_at | HS.146022 | ACMSD | aminocarboxymuconate semialdehyde decarboxylase | 571 | −1.08 | 1.19 | −1.38 | −2.39 |
| 205364_at | HS.444959 | ACOX2 | acyl-Coenzyme A oxidase 2, branched chain | 276 | −1.02 | 1.03 | −1.46 | −2.52 |
| 202422_s_at | HS.268785 | ACSL4 | acyl-CoA synthetase long-chain family member 4 | 1125 | −1.03 | 1.00 | 1.40 | 1.53 |
| 205745_x_at | HS.404914 | ADAM17 | a disintegrin and metalloproteinase domain 17 (tumor necrosis factor, alpha, converting enzyme) | 227 | −1.01 | −1.02 | 1.18 | 1.67 |
| 213532_at | HS.404914 | ADAM17 | a disintegrin and metalloproteinase domain 17 (tumor necrosis factor, alpha, converting enzyme) | 259 | −1.02 | −1.08 | 1.11 | 1.49 |
| 222930_s_at | HS.461532 | AGMAT | agmatine ureohydrolase (agmatinase) | 198 | −1.04 | 1.03 | −1.57 | −4.02 |
| 229229_at | HS.34494 | AGXT2 | alanine-glyoxylate aminotransferase 2 | 858 | −1.08 | 1.34 | −1.09 | −2.15 |
| 227530_at | HS.371240 | AKAP12 | A kinase (PRKA) anchor protein (gravin) 12 | 778 | 1.00 | 1.07 | 1.06 | 1.99 |
| 218487_at | HS.1227 | ALAD | aminolevulinate, delta-, dehydratase | 499 | −1.03 | 1.02 | −1.58 | −2.42 |
| 211298_s_at | | ALB | albumin | 444 | 1.07 | 1.91 | −4.01 | −9.43 |
| 208950_s_at | HS.483239 | ALDH7A1 | aldehyde dehydrogenase 7 family, member A1 | 838 | −1.02 | −1.01 | −1.37 | −1.72 |
| 208951_at | HS.483239 | ALDH7A1 | aldehyde dehydrogenase 7 family, member A1 | 438 | −1.01 | −1.01 | −1.62 | −2.19 |
| 220148_at | HS.486520 | ALDH8A1 | aldehyde dehydrogenase 8 family, member A1 | 1505 | −1.20 | 1.32 | −1.14 | −1.85 |
| 201612_at | HS.2533 | ALDH9A1 | aldehyde dehydrogenase 9 family, member A1 | 3300 | 1.01 | −1.07 | −1.22 | −1.55 |
| 205682_x_at | HS.534468 | APOM | apolipoprotein M | 633 | −1.05 | −1.08 | −1.84 | −3.82 |
| 205673_s_at | HS.19404 | ASB9 | ankyrin repeat and SOCS box-containing 9 | 131 | −1.03 | 1.06 | −1.78 | −3.82 |
| 219902_at | HS.114172 | BHMT2 | betaine-homocysteine methyltransferase 2 | 1053 | −1.10 | 1.04 | −1.40 | −2.81 |
| 204741_at | HS.505202 | BICD1 | Bicaudal D homolog 1 (*Drosophila*) | 146 | 1.02 | 1.10 | 1.67 | 1.86 |
| 223824_at | HS.149849 | C10ORF59 | chromosome 10 open reading frame 59 | 345 | −1.02 | −1.13 | −1.30 | −1.70 |
| 225687_at | HS.472716 | C20ORF129 | chromosome 20 open reading frame 129 | 107 | 1.04 | −1.05 | −1.65 | −2.32 |
| 228560_at | HS.476358 | CACNA1D | calcium channel, voltage-dependent, L type, alpha 1D | 418 | −1.13 | 1.31 | −1.11 | −1.49 |
| 216903_s_at | HS.524367 | CBARA1 | calcium binding atopy-related autoantigen 1 | 365 | −1.03 | −1.05 | −1.39 | −1.96 |

TABLE 2-continued

Biomarker Genes of the Invention

| Affymetrix Probeset ID | UNIGENE | Symbol | Gene Name | Raw | Normalized Values | | | |
|---|---|---|---|---|---|---|---|---|
| | | | | | normal | CR 1 | CR 2 | CR 3 |
| 224027_at | HS.334633 | CCL28 | chemokine (C-C motif) ligand 28 | 27 | −1.09 | −1.09 | 1.53 | 2.35 |
| 1559590_at | HS.126688 | CHDH | choline dehydrogenase | 35 | −1.36 | 1.20 | 1.09 | −1.64 |
| 218252_at | HS.444028 | CKAP2 | cytoskeleton associated protein 2 | 190 | −1.00 | −1.27 | −1.25 | −1.46 |
| 212091_s_at | HS.474053 | COL6A1 | collagen, type VI, alpha 1 | 58 | −1.17 | −1.17 | −2.25 | −1.71 |
| 208146_s_at | HS.233389 | CPVL | carboxypeptidase, vitellogenic-like | 951 | 1.01 | −1.04 | 1.20 | 1.58 |
| 203915_at | HS.77367 | CXCL9 | chemokine (C—X—C motif) ligand 9 | 831 | 1.14 | −1.05 | −1.11 | −2.43 |
| 206878_at | HS.113227 | DAO | D-amino-acid oxidase | 202 | −1.04 | 1.11 | −1.93 | −4.55 |
| 230175_s_at | HS.203691 | DCBLD2 | discoidin, CUB and LCCL domain containing 2 | 364 | 1.01 | −1.06 | 1.11 | 1.34 |
| 217973_at | HS.9857 | DCXR | dicarbonyl/L-xylulose reductase | 907 | −1.11 | −1.30 | −1.47 | −3.56 |
| 204977_at | HS.525115 | DDX10 | DEAD (Asp-Glu-Ala-Asp) box polypeptide 10 | 343 | 1.03 | 1.02 | −1.47 | −1.97 |
| 232381_s_at | HS.520106 HS.212360 | DNAH5 | dynein, axonemal, heavy polypeptide 5 | 147 | 1.05 | 1.28 | 2.65 | 1.97 |
| 226281_at | HS.234074 | DNER | delta-notch-like EGF repeat-containing transmembrane | 484 | −1.13 | −1.07 | 1.58 | 1.49 |
| 203716_s_at | HS.368912 | DPP4 | dipeptidylpeptidase 4 (CD26, adenosine deaminase complexing protein 2) | 121 | −1.05 | 1.20 | −1.56 | −2.31 |
| 219298_at | HS.22242 | ECHDC3 | enoyl Coenzyme A hydratase domain containing 3 | 473 | −1.04 | −1.05 | −1.39 | −2.33 |
| 224189_x_at | HS.502306 | EHF | ets homologous factor | 24 | −1.14 | 1.19 | 2.14 | 1.95 |
| 209368_at | HS.212088 | EPHX2 | epoxide hydrolase 2, cytoplasmic | 334 | −1.17 | −1.26 | −1.50 | −2.64 |
| 211398_at | HS.533683 | FGFR2 | fibroblast growth factor receptor 2 | 21 | −1.04 | −1.05 | −1.84 | −2.46 |
| 211399_at | HS.533683 | FGFR2 | fibroblast growth factor receptor 3 | 27 | −1.15 | 1.09 | −1.51 | −2.87 |
| 211400_at | HS.533683 | FGFR2 | fibroblast growth factor receptor 4 | 16 | −1.46 | −1.28 | −1.43 | −2.01 |
| 230842_at | HS.533683 | FGFR2 | fibroblast growth factor receptor 5 | 11 | 1.12 | 1.06 | −2.66 | −2.18 |
| 219118_at | HS.438695 | FKBP11 | FK506 binding protein 11, 19 kDa | 85 | 1.00 | −1.00 | 1.96 | 2.19 |
| 1559011_at | HS.462392 | FLJ13773 | hypothetical protein FLJ13773 | 25 | −1.21 | 1.12 | 1.79 | 1.86 |
| 227417_at | HS.369042 | FLJ20605 | hypothetical protein FLJ20605 | 803 | −1.04 | 1.05 | −1.47 | −2.22 |
| 228397_at | HS.158783 | FLJ20618 | hypothetical protein FLJ20618 | 254 | −1.02 | 1.01 | 1.46 | 2.21 |
| 221925_s_at | HS.370147 | FLJ22490 | hypothetical protein FLJ22490 | 51 | −1.01 | 1.01 | −1.34 | −1.45 |
| 238593_at | HS.292088 | FLJ22531 | hypothetical protein FLJ22531 | 402 | −1.12 | 1.39 | 1.64 | 1.86 |
| 207876_s_at | HS.58414 | FLNC | filamin C, gamma (actin binding protein 280) | 495 | 1.49 | 1.20 | 1.14 | 1.98 |
| 215062_at | HS.149566 | FMNL2 | formin-like 2 | 65 | −1.04 | 1.38 | 1.51 | 1.82 |
| 206263_at | HS.386502 | FMO4 | flavin containing monooxygenase 4 | 388 | −1.09 | −1.11 | −1.59 | −3.50 |
| 1568955_at | | FNBP2 | LOC391156 | 358 | −1.04 | −1.14 | 1.21 | 2.35 |
| 226962_at | HS.529439 | FRBZ1 | FRBZ1 protein | 574 | 1.00 | 1.13 | 1.18 | 1.45 |
| 214093_s_at | HS.269099 | FUBP1 | far upstream element (FUSE) binding protein 1 | 277 | −1.04 | −1.02 | 1.19 | 2.00 |
| 216010_x_at | HS.169238 | FUT3 | fucosyltransferase 3 (galactoside 3(4)-L-fucosyltransferase, Lewis blood group included) | 32 | −1.24 | −1.33 | −1.52 | −2.66 |
| 228238_at | HS.531856 | GAS5 | growth arrest-specific 5 | 260 | 1.01 | 1.07 | 1.25 | 1.83 |
| 213133_s_at | HS.435741 HS.546256 | GCSH | glycine cleavage system protein H (aminomethyl carrier) | 443 | −1.01 | −1.14 | −1.42 | −1.85 |
| 230025_at | HS.444663 | GJC1 | gap junction protein, chi 1, 31.9 kDa (connexin 31.9) | 102 | 1.01 | −1.13 | −1.24 | −1.52 |
| 202382_s_at | HS.278500 | GNPDA1 | glucosamine-6-phosphate deaminase 1 | 690 | −1.03 | −1.06 | −1.30 | −2.10 |
| 224997_x_at | HS.533566 | H19 | H19, imprinted maternally expressed untranslated mRNA | 336 | 1.28 | 1.10 | −1.04 | 1.48 |
| 205012_s_at | HS.157394 HS.513265 | HAGH | hydroxyacylglutathione hydrolase | 455 | −1.06 | −1.13 | −1.56 | −2.26 |
| 226137_at | HS.77558 HS.546885 | HMGN3 | high mobility group nucleosomal binding domain 3 | 559 | 1.01 | −1.03 | 1.20 | 1.88 |
| 204934_s_at | HS.182385 | HPN | hepsin (transmembrane protease, serine 1) | 436 | −1.20 | −1.04 | −1.25 | −2.06 |
| 210253_at | HS.90753 | HTATIP2 | HIV-1 Tat interactive protein 2, 30 kDa | 231 | −1.04 | 1.00 | 1.28 | 1.39 |
| 235549_at | HS.148741 | IBRDC2 | IBR domain containing 2 | 28 | −1.36 | 1.03 | 1.31 | 2.04 |
| 202410_x_at | HS.373908 HS.523414 | IGF2 | insulin-like growth factor 2 (somatomedin A) | 10 | 1.04 | 1.09 | −1.37 | −1.32 |
| 210881_s_at | HS.373908 HS.523414 | IGF2 | insulin-like growth factor 2 (somatomedin A) | 7 | 1.18 | 1.06 | −1.20 | 1.03 |
| 1553594_a_at | HS.37062 HS.515247 | INSL3, JAK3 | Janus kinase 3 (a protein tyrosine kinase, leukocyte) | 108 | −1.07 | −1.26 | −1.30 | −1.68 |
| 210840_s_at | HS.430551 | IQGAP1 | IQ motif containing GTPase activating protein 1 | 566 | 1.05 | −1.10 | 1.39 | 1.71 |
| 203752_s_at | HS.2780 | JUND | jun D proto-oncogene | 1456 | −1.00 | 1.02 | 1.09 | 1.36 |
| 211806_s_at | HS.411299 | KCNJ15 | potassium inwardly-rectifying channel, subfamily J, member 15 | 303 | −1.03 | −1.12 | −1.44 | −1.82 |
| 238428_at | HS.411299 | KCNJ15 | potassium inwardly-rectifying channel, subfamily J, member 15 | 211 | −1.04 | 1.04 | −1.45 | −1.64 |

TABLE 2-continued

Biomarker Genes of the Invention

| Affymetrix Probeset ID | UNIGENE | Symbol | Gene Name | Raw | Normalized Values | | | |
|---|---|---|---|---|---|---|---|---|
| | | | | | normal | CR 1 | CR 2 | CR 3 |
| 220116_at | HS.98280 | KCNN2 | potassium intermediate/small conductance calcium-activated channel, subfamily N, member 2 | 60 | −1.10 | −1.05 | −2.39 | −3.45 |
| 215268_at | HS.472475 | KIAA0754 | KIAA0754 protein | 88 | −1.03 | 1.18 | 1.97 | 1.94 |
| 213913_s_at | HS.192492 | KIAA0984 | KIAA0984 protein | 125 | −1.02 | 1.05 | 1.26 | 1.69 |
| 244370_at | HS.124128 | KIAA2022 | KIAA2022 protein | 188 | −1.10 | −1.03 | 1.37 | 1.52 |
| 202962_at | HS.444767 | KIF13B | kinesin family member 13B | 598 | −1.08 | 1.03 | −1.06 | −1.56 |
| 216568_x_at | HS.533782 | KRT8 | keratin 8 | 24 | −1.12 | −1.06 | 1.66 | 2.51 |
| 242424_at | HS.370457 | LETMD1 | LETM1 domain containing 1 | 51 | −1.18 | 1.46 | 2.70 | 2.40 |
| 227285_at | HS.54680 | LOC148523 | hypothetical protein BC017397 | 194 | −1.07 | −1.34 | −1.68 | −2.34 |
| 228857_at | HS.537654 | LOC285831 | hypothetical protein LOC285831 | 152 | 1.01 | 1.06 | −1.25 | −1.32 |
| 230554_at | HS.298252 | LOC348158 | hypothetical protein LOC123876 | 4581 | −1.25 | 1.38 | −1.07 | −1.58 |
| 231001_at | HS.32478 | LOC387758 | similar to RIKEN cDNA 1110018M03 | 214 | 1.01 | 1.15 | 1.57 | 2.06 |
| 227372_s_at | HS.489237 | LOC55971 | insulin receptor tyrosine kinase substrate | 211 | −1.05 | −1.04 | 1.33 | 1.42 |
| 230931_at | HS.439074 HS.449164 | LPAL2 | lipoprotein, Lp(a)-like 2 | 271 | −1.02 | 1.34 | −1.52 | −6.27 |
| 230863_at | HS.470538 | LRP2 | low density lipoprotein-related protein 2 | 1433 | −1.21 | 1.34 | −1.15 | −1.46 |
| 243170_at | HS.543294 | LRRC2 | leucine rich repeat containing 2 | 101 | −1.04 | 1.02 | −1.30 | −1.38 |
| 236322_at | HS.197043 | MAN1C1 | mannosidase, alpha, class 1C, member 1 | 112 | −1.04 | 1.20 | 1.68 | 2.07 |
| 203929_s_at | HS.546914 HS.101174 | MAPT | microtubule-associated protein tau | 235 | 1.01 | 1.08 | −1.15 | −1.87 |
| 213333_at | HS.520967 | MDH2 | malate dehydrogenase 2, NAD (mitochondrial) | 347 | 1.01 | −1.14 | −1.22 | −1.56 |
| 1553715_s_at | HS.417710 | MGC15416 | hypothetical protein MGC15416 | 543 | −1.05 | −1.15 | −1.19 | −1.97 |
| 229596_at | HS.424907 | MGC35366 | hypothetical protein MGC35366 | 170 | −1.08 | 1.27 | −1.70 | −2.98 |
| 212462_at | HS.35758 | MYST4 | MYST histone acetyltransferase (monocytic leukemia) 4 | 323 | −1.00 | 1.06 | 1.12 | 1.42 |
| 217593_at | HS.235390 | null | hypothetical protein FLJ12895 | 143 | −1.08 | 1.16 | 1.58 | 1.87 |
| 219049_at | HS.387794 | null | chondroitin beta1,4 N-acetylgalactosaminyltransferase | 348 | −1.03 | −1.29 | 1.53 | 2.47 |
| 238469_at | HS.16512 | OGFRL1 | opioid growth factor receptor-like 1 | 48 | −1.01 | −1.13 | 1.18 | 1.70 |
| 1558017_s_at | HS.406074 | PAWR | PRKC, apoptosis, WT1, regulator | 193 | −1.05 | 1.45 | 1.58 | 1.98 |
| 213263_s_at | HS.546271 | PCBP2 | poly(rC) binding protein 2 | 383 | −1.05 | 1.02 | −1.36 | −1.82 |
| 232099_at | HS.147674 | PCDHB16 | protocadherin beta 16 | 159 | −1.01 | 1.07 | 1.54 | 2.31 |
| 205380_at | HS.143293 HS.444751 | PDZK1 | PDZ domain containing 1 | 2598 | −1.18 | 1.17 | −1.23 | −1.79 |
| 218025_s_at | HS.15250 | PEC1 | peroxisomal D3,D2-enoyl-CoA isomerase | 1404 | −1.09 | −1.18 | −1.47 | −2.30 |
| 202108_at | HS.36473 | PEPD | peptidase D | 1240 | −1.06 | −1.11 | −1.50 | −2.80 |
| 202464_s_at | HS.195471 | PFKFB3 | 6-phosphofructo-2-kinase/fructose-2,6-biphosphatase 3 | 2256 | −1.01 | 1.07 | 1.50 | 2.34 |
| 220944_at | HS.58356 | PGLYRP4 | peptidoglycan recognition protein 4 | 60 | −1.01 | −1.01 | −1.54 | −1.75 |
| 232530_at | HS.478230 | PLD1 | phospholipase D1, phophatidylcholine-specific | 21 | −1.16 | 1.20 | 2.66 | 4.96 |
| 232212_at | HS.334649 HS.233495 | PLEKHA8 | pleckstrin homology domain containing, family A (phosphoinositide binding specific) member 8 | 45 | −1.13 | −1.33 | −1.57 | −2.35 |
| 241916_at | HS.130759 | PLSCR1 | phospholipid scramblase 1 | 130 | −1.00 | 1.14 | 1.56 | 1.96 |
| 222653_at | HS.514278 | PNPO | pyridoxine 5′-phosphate oxidase | 370 | −1.05 | −1.12 | −1.42 | −2.01 |
| 236044_at | HS.40479 | PPAPDC1 | phosphatidic acid phosphatase type 2 domain containing 1 | 187 | 1.03 | 1.04 | −1.43 | −1.76 |
| 219195_at | HS.527078 | PPARGC1A | peroxisome proliferative activated receptor, gamma, coactivator 1, alpha | 1110 | −1.03 | 1.02 | 1.10 | 1.22 |
| 206346_at | HS.368587 | PRLR | prolactin receptor | 88 | 1.01 | 1.04 | −1.52 | −3.78 |
| 204304_s_at | HS.479220 | PROM1 | prominin 1 | 1015 | −1.16 | 1.18 | 1.85 | 3.08 |
| 209123_at | HS.75438 | QDPR | quinoid dihydropteridine reductase | 855 | −1.05 | −1.10 | −1.49 | −2.84 |
| 225188_at | HS.471162 | RAPH1 | Ras association (RalGDS/AF-6) and pleckstrin homology domains 1 | 1025 | 1.01 | −1.04 | 1.27 | 1.57 |
| 235144_at | HS.129136 | RASEF | RAS and EF hand domain containing | 209 | −1.01 | 1.03 | 1.20 | 1.55 |
| 203344_s_at | HS.546282 | RBBP8 | retinoblastoma binding protein 8 | 1153 | −1.03 | −1.15 | 1.22 | 1.78 |
| 240245_at | HS.221436 | RBMS3 | RNA binding motif, single stranded interacting protein | 142 | 1.01 | 1.02 | 1.60 | 1.74 |
| 217775_s_at | HS.226007 | RDH11 | retinol dehydrogenase 11 (all-trans and 9-cis) | 573 | −1.06 | −1.21 | −1.14 | −1.68 |
| 216621_at | HS.306307 | ROCK1 | Rho-associated, coiled-coil containing protein kinase 1 | 68 | 1.02 | 1.32 | 1.50 | 1.66 |

TABLE 2-continued

Biomarker Genes of the Invention

| Affymetrix Probeset ID | UNIGENE | Symbol | Gene Name | Raw | Normalized Values | | | |
|---|---|---|---|---|---|---|---|---|
| | | | | | normal | CR 1 | CR 2 | CR 3 |
| 206169_x_at | HS.474970 | RoXaN | rotavirus X protein associated with NSP3 | 429 | 1.03 | 1.08 | 1.37 | 1.65 |
| 225150_s_at | HS.192854 | RTKN | rhotekin | 172 | −1.10 | −1.03 | −1.37 | −2.27 |
| 229273_at | HS.135787 | SALL1 | sal-like 1 (*Drosophila*) | 395 | −1.10 | −1.04 | −1.03 | 1.03 |
| 205075_at | HS.159509 | SERPINF2 | serine (or cysteine) proteinase inhibitor, clade F (alpha-2 antiplasmin, pigment epithelium derived factor), member 2 | 139 | −1.12 | 1.16 | −1.02 | −1.67 |
| 214016_s_at | HS.355934 | SFPQ | splicing factor proline/glutamine rich (polypyrimidine tract binding protein associated) | 1584 | 1.02 | 1.17 | 1.60 | 2.07 |
| 213590_at | HS.369554 | SLC16A5 | solute carrier family 16 (monocarboxylic acid transporters), member 5 | 258 | −1.07 | −1.07 | 1.42 | 1.67 |
| 208177_at | HS.936 | SLC34A1 | solute carrier family 34 (sodium phosphate), member 1 | 176 | −1.05 | 1.75 | −1.41 | −4.40 |
| 238177_at | HS.481478 | SLC6A19 | solute carrier family 6 (neurotransmitter transporter), member 19 | 143 | −1.26 | 1.45 | −1.54 | −3.65 |
| 220135_s_at | HS.408567 | SLC7A9 | solute carrier family 7 (cationic amino acid transporter, y+ system), member 9 | 1017 | −1.15 | 1.36 | −1.29 | −2.76 |
| 222071_s_at | HS.127648 | SLCO4C1 | solute carrier organic anion transporter family, member 4C1 | 1060 | −1.22 | −1.01 | −1.24 | −1.38 |
| 203021_at | HS.517070 | SLPI | secretory leukocyte protease inhibitor (antileukoproteinase) | 433 | 1.03 | −1.02 | 1.67 | 2.37 |
| 233713_at | HS.66170 | SMYD2 | SET and MYND domain containing 2 | 99 | 1.04 | 1.22 | 1.27 | 2.02 |
| 210715_s_at | HS.31439 | SPINT2 | serine protease inhibitor, Kunitz type, 2 | 1265 | −1.07 | 1.03 | −1.01 | 1.10 |
| 212459_x_at | HS.186512 | SUCLG2 | succinate-CoA ligase, GDP-forming, beta subunit | 1428 | −1.02 | −1.04 | −1.24 | −1.47 |
| 227480_at | HS.131819 | SUSD2 | sushi domain containing 2 | 264 | 1.01 | 1.07 | −1.74 | −3.78 |
| 203084_at | HS.1103 | TGFB1 | transforming growth factor, beta 1 (Camurati-Engelmann disease) | 40 | −1.10 | −1.37 | −1.52 | −1.61 |
| 203085_s_at | HS.1103 | TGFB1 | transforming growth factor, beta 1 (Camurati-Engelmann disease) | 7 | 1.23 | 1.06 | −1.00 | 1.02 |
| 204565_at | HS.9676 | THEM2 | thioesterase superfamily member 2 | 239 | −1.07 | −1.14 | −1.75 | −2.41 |
| 212701_at | HS.511686 | TLN2 | talin 2 | 203 | −1.04 | 1.17 | −1.45 | −2.27 |
| 226860_at | HS.7337 | TMEM19 | transmembrane protein 19 | 383 | −1.04 | −1.10 | −1.37 | −1.73 |
| 200822_x_at | HS.524219 | TPI1 | triosephosphate isomerase 1 | 2029 | −1.00 | −1.19 | −1.26 | −1.44 |
| 211700_s_at | HS.434971 | TRO | trophinin | 132 | −1.12 | 1.09 | 1.80 | 2.20 |
| 208958_at | HS.154023 | TXNDC4 | thioredoxin domain containing 4 (endoplasmic reticulum) | 65 | 1.02 | 1.12 | 1.23 | 1.66 |
| 233155_at | HS.128427 | UPP2 | uridine phosphorylase 2 | 52 | −1.03 | −1.03 | −1.81 | −3.12 |
| 244622_at | HS.314338 | WDR9 | WD repeat domain 9 | 38 | −1.02 | 1.30 | 1.50 | 2.35 |
| 1555192_at | HS.489722 | ZNF277 | zinc finger protein (C2H2 type) 277 | 20 | −1.06 | −1.08 | 1.48 | 1.72 |
| 235493_at | HS.434401 | ZNF638 | zinc finger protein 638 | 156 | 1.01 | 1.17 | 1.52 | 1.38 |
| 205594_at | HS.463375 | ZNF652 | zinc finger protein 652 | 151 | 1.02 | −1.01 | 1.14 | 1.74 |
| 1569477_at | | | | 148 | 1.04 | 1.34 | 1.47 | 1.68 |
| 1569578_at | | | | 49 | −1.02 | 1.21 | 1.77 | 2.10 |
| 227955_s_at | | | | 547 | −1.02 | 1.06 | 1.44 | 1.96 |
| 230168_at | | | | 103 | −1.05 | 1.12 | 1.16 | 1.71 |
| 230332_at | | | | 260 | 1.06 | 1.20 | 1.35 | 1.58 |
| 233607_at | | | | 503 | 1.04 | 1.38 | 1.85 | 1.79 |
| 236685_at | | | | 218 | 1.05 | 1.19 | 1.33 | 1.67 |
| 237317_at | | | | 99 | 1.06 | 1.35 | 1.95 | 1.76 |
| 238299_at | | | | 90 | −1.05 | 1.12 | 1.25 | 1.66 |
| 239066_at | | | | 333 | −1.03 | 1.23 | 1.45 | 2.09 |
| 239264_at | | | | 159 | 1.06 | 1.28 | 1.57 | 1.66 |
| 239907_at | | | | 264 | −1.00 | 1.27 | 1.74 | 1.74 |
| 240800_x_at | | | | 64 | −1.06 | 1.15 | 1.32 | 1.33 |
| 242967_at | | | | 107 | −1.17 | 1.21 | −1.71 | −2.48 |
| 243591_at | | | | 116 | −1.05 | 1.15 | 1.99 | 2.86 |
| 243598_at | | | | 50 | −1.09 | 1.15 | 1.71 | 1.72 |
| 244803_at | | | | 129 | −1.04 | 1.20 | 1.57 | 1.79 |

Accordingly, in one aspect the invention pertains to using a recognition signature comprising one or more of the genes shown in Table 2 to indicate transplant rejection, in particular CAN rejection of a transplanted organ. In one embodiment, the invention pertains to using a recognition signature comprising a combination of a plurality of genes shown in Table 2 to indicate transplant rejection, in particular CAN rejection of a transplanted organ.

Clinical Features of CAN

Chronic transplant dysfunction is a phenomenon in solid organ transplants displaying a gradual deterioration of graft function months to years after transplantation, eventually leading to graft failure, and which is accompanied by characteristic histological features. Clinically, chronic allograft nephropathy in kidney grafts (i.e., CAN) manifests itself as a slowly progressive decline in glomerular filtration rate, usually in conjunction with proteinuria and arterial hypertension.

The cardinal histomorphologic feature of CAN in all parenchymal allografts is fibroproliferative endarteritis. The vascular lesion affects the whole length of the arteries in a patchy pattern. There is concentric myointimal proliferation resulting in fibrous thickening and the characteristic 'onion skin' appearance of the intima in small arteries. Other findings include endothelial swelling, foam cell accumulation, disruption of the internal elastic lamina, hyalinosis and medial thickening, and presence of subendothelial T-lymphocytes and macrophages (Hruban R H, et al., Am J Pathol 137(4):871-82 (1990)). In addition, a persistent focal perivascular inflammation is often seen.

In addition to vascular changes, kidneys undergoing CAN also show interstitial fibrosis, tubular atrophy, and glumerulopathy. Chronic transplant glumerolopathy—duplication of the capillary walls and mesangial matrix increase—has been identified as a highly specific feature of kidneys with CAN (Solez K, Clin Transplant.; 8(3 Pt 2):345-50 (1994)). Less specific lesions are glomerular ischemic collapse, tubular atrophy, and interstitial fibrosis. Furthermore, peritubular capillary basement splitting and laminations are associated with late decline of graft function (Monga M, et al., Ultrastruct Pathol. 14(3):201-9 (1990)). The criteria for histological diagnosis of CAN in kidney allografts are internationally standardized in the Banff 97 scheme for Renal Allograft Pathology (Racusen L C, et al., Kidney Int. 55(2):713-23 (1999)); (adopted from Kouwenhoven et al., Transpl Int. 2000; 13(6):385-401. 2000). Table 3 summarizes the Banff 97 criteria for CAN (Racusen L C, et al., Kidney Int. 55(2): 713-23 (1999)).

TABLE 3

Grading of Histopathological Findings
of Chronic Allograft Nephropathy (CAN)

| Grade | Histopathological Findings |
|---|---|
| I - mild | Mild interstitial fibrosis and tubular atrophy without (a) or with (b) specific changes suggesting chronic rejection |
| II - moderate | Moderate interstitial fibrosis and tubular atrophy (a) or (b) |
| III - severe | Severe interstitial fibrosis and tubular atrophy and tubular loss (a) or (b) |

For Banff 97, an "adequate" specimen is defined as a biopsy with 10 or more glumeruli and at least two arteries. Two working hypotheses are proposed to understand the process of CAN (Kouwenhoven et al., Transpl Int. 2000; 13(6): 385-401. 2000). The first and probably the most important set of risk factors have been lumped under the designation of "alloantigen-dependent", immunological or rejection-related factors. Among these, late onset and increased number of acute rejection episodes; younger recipient age; male-to-female sex mismatch; a primary diagnosis of autoimmune hepatitis or biliary disease; baseline immunosuppression and non-caucasian recipient race have all been associated with an increased risk of developing chronic rejection. More specifically, (a) histoincompatibility: long-term graft survival appear to be strongly correlated with their degree of histocompatibility matching between donor and recipient; (b) Acute rejections: onset, frequency, and severity of acute rejection episodes are independent risk factors of CAN. Acute rejection is the most consistently identified risk factor for the occurrence of CAN; (c) Suboptimal immunosuppression due to too low maintenance dose of cyclosporine or non-compliance; and (d) Anti-donor specific antibodies: many studies have shown that following transplantation, the majority of patients produce antibodies.

The second set of risk factors are referred to as "non-alloantigen-dependent" or "non-immunological" risk factors that also contribute to the development of chronic rejection include advanced donor age, pre-existing atherosclerosis in the donor organ, and prolonged cold ischemic time. Non-alloimmune responses to disease and injury, such as ischemia, can cause or aggravate CAN. More specifically, (a) recurrence of the original disease, such as glomerulonephritis; (b) consequence of the transplantation surgical injury; (c) duration of ischemia: intimal hyperplasia correlates with duration of ischemia; (d) kidney grafts from cadavers versus those from living related and unrelated donors; (e) viral infections: CMV infection directly affects intercellular adhesion molecules such as ICAM-1; (f) hyperlipidemia; (g) hypertension; (h) age; (i) gender: the onset of transplant arterosclerosis was earlier in male than in female; (j) race; and (k) the amount of functional tissue—reduced number of nephrons and hyperfiltration.

CAN is characterized by morphological evidence of destruction of the transplanted organ. The common denominator of all parenchymal organs is the development of intimal hyperplasia. T cells and macrophages are the predominant graft-invading cell types, with an excess of $CD4^+$ over $CD8^+$ T cells. Increased expression of adhesion molecules (ICAM-1, VCAM-1) and MHC antigens are seen in allografts with CAN, and increased TGF-$\beta$ is frequently found. A short description of the route through which a graft may develop CAN follows:

Endothelial Cell Activation by Ischemia, Surgical Manipulation, and Reperfusion Injury.

In consequence, the endothelial cells produce oxygen free radicals and they release increased amounts of the cytokines IL-1, IL-6, IFN-$\gamma$, TNF-$\alpha$ and the chemokines IL-8, macrophage chemoattractant protein 1 (MCP-1), macrophage inflammatory protein 1$\alpha$ and 1$\beta$ (MIP-1$\alpha$, MIP-1 $\beta$), colony stimulating factors, and multiple growth factors such as, platelet derived growth factor (PDGF), insulin like growth factor 1 (IGF-1), transforming growth factor $\beta$ (TGF-$\beta$), and prothrombotic molecules such as tissue factor and plasminogen activator inhibitor (PAI). These cytokines activate the migration of neutrophils, monocytes/macrophages and T-lymphocytes to the site of injury where they interact with the endothelial cells by means of adhesion molecules, including ICAM-1, VCAM-1, P- and E-selectin. The increased expression of these adhesion molecules is induced by the cytokines IL-1$\beta$, IFN-$\gamma$, and TNF-$\alpha$. Extravasation of leucocytes is facilitated by activated complement and oxygen-free radicals that increase the permeability between endothelial cells.

Limitations to Current Clinical Approaches for can Diagnosis

The differentiation of the diagnosis of rejection, e.g., CAN, from other etiologies for graft dysfunction and institution of effective therapy is a complex process because: (a) the percutaneous core needle biopsy of grafts, the best of available current tools to diagnose rejection is performed usually after the "fact", i.e., graft dysfunction and graft damage (irreversible in some instances) are already present, (b) the morphological analysis of the graft provides modest clues with respect to the potential for reversal of a given rejection episode, and minimal clues regarding the likelihood of recurrence ("rebound"), and (c) the mechanistic basis of the rejection phenomenon, a prerequisite for the design of therapeutic strategies, is poorly defined by current diagnostic indices, including morphologic features of rejection.

The diagnosis of, for example, renal allograft rejection is made usually by the development of graft dysfunction (e.g., an increase in the concentration of serum creatinine) and morphologic evidence of graft injury in areas of the graft also manifesting mononuclear cell infiltration. Two caveats apply, however, to the use of abnormal renal function as an indicator of the rejection process: first, deterioration in renal function is not always available as a clinical clue to diagnose rejection since many of the cadaveric renal grafts suffer from acute (reversible) renal failure in the immediate post-transplantation period due to injury from harvesting and ex vivo preservation procedures. Second, even when immediately unimpaired renal function is present, graft dysfunction might develop due to a non-immunologic cause, such as immunosuppressive therapy itself.

For example, cyclosporine (CsA) nephrotoxicity, a complication that is not readily identified solely on the basis of plasma/blood concentrations of CsA, is a common complication. The clinical importance of distinguishing rejection from CsA nephrotoxicity cannot be overemphasized since the therapeutic strategies are diametrically opposite: escalation of immunosuppressants for rejection, and reduction of CsA dosage for nephrotoxicity.

The invention is based, in part, on the observation that increased or decreased expression of on or more genes and/or the encoded proteins is associated with certain graft rejection states. As a result of the data described herein, methods are now available for the rapid and reliable diagnosis of acute and chronic rejection, even in cases where allograft biopsies show only mild cellular infiltrates. Described herein is an analysis of genes that are modulated (e.g., up-regulated or down-regulated) simultaneously and which provide a molecular signature to accurately detect transplant rejection and/or grade the severity or progression of transplant rejection.

The invention further provides classic molecular methods and large scale methods for measuring expression of suitable biomarker genes. The methods described herein are particularly useful for detecting chronic transplant rejection and preferably early chronic transplant rejection. In one embodiment, the chronic transplant rejection is the result of CAN. Most typically, the subject (i.e., the recipient of a transplant) is a mammal, such as a human. The transplanted organ can include any transplantable organ or tissue, for example kidney, heart, lung, liver, pancreas, bone, bone marrow, bowel, nerve, stem cells (or stem cell-derived cells), tissue component and tissue composite. In a preferred embodiment, the transplant is a kidney transplant.

The methods described herein are useful to assess the efficacy of anti-rejection therapy. Such methods involve comparing the pre-administration magnitude of the transcripts of the biomarker genes to the post-administration magnitude of the transcripts of the same genes, where a post-administration magnitude of the transcripts of the genes that is less than the pre-administration magnitude of the transcripts of the same genes indicates the efficacy of the anti-rejection therapy. Any candidates for prevention and/or treatment of transplant rejection, (such as drugs, antibodies, or other forms of rejection or prevention) can be screened by comparison of magnitude of biomarker expression before and after exposure to the candidate. In addition, valuable information can be gathered in this manner to aid in the determination of future clinical management of the subject upon whose biological material the assessment is being performed. The assessment can be performed using a sample from the subject, using the methods described herein for determining the magnitude of gene expression of the biomarker genes. Analysis can further comprise detection of an infectious agent.

Biological Pathways Associated with Biomarkers of the Invention

Biomarkers of the present invention identify selected biological pathways affected by CAN and, as such, these biological pathways are of relevance to solid organ allograft nephropathy. Indeed, this analysis revealed robust biomarker signatures for select biological pathways which can represent gene clusters. Such biological pathways include, but are not limited to, e.g., the biological pathways presented in Example I in the section entitled, "Select CAN-Associated Genes of the Invention."

The advent of large scale gene expression analysis has revealed that groups of genes are often expressed together in a coordinated manner. For example, whole genome expression analysis in the yeast *Saccharomyces cerevisiae* showed coordinate regulation of metabolic genes during a change in growth conditions known as the diauxic shift (DiRisi et al., 1997, Science 278:680-686; Eisen et al., 1998, PNAS 95:14863-14868). The diauxic shift occurs when yeast cells fermenting glucose to ethanol exhaust the glucose in the media and begin to metabolize the ethanol. In the presence of glucose, genes of the glycolytic pathway are expressed and carry out the fermentation of glucose to ethanol. When the glucose is exhausted, yeast cells must metabolize the ethanol, a process that depends heavily on the Krebs cycle and respiration.

Accordingly, the expression of glycolysis genes decreases, and the expression of Krebs cycle and respiratory genes increases in a coordinate manner. Similar coordinate gene regulation has been found in various cancer cells Genes encoding proteins involved in cell cycle progression and DNA synthesis are often coordinately overexpressed in cancerous cells (Ross et al., 2000, Nature Genet. 24:227-235; Perou et al., 1999, PNAS 96:9212-9217; Perou et al., 2000, Nature 406:747-752).

The coordinate regulation of genes is logical from a functional point of view. Most cellular processes require multiple genes, for example: glycolysis, the Krebs cycle, and cell cycle progression are all multi-gene processes. Coordinate expression of functionally related genes is therefore essential to permit cells to perform various cellular activities. Such groupings of genes can be called "gene clusters" (Eisen et al., 1998, PNAS 95:14863-68). Likewise, the coordinate expression of functionally related genes in CAN, and specifically, chronic rejection are also within the scope of the invention.

Clustering of gene expression is not only a functional necessity, but also a natural consequence of the mechanisms of transcriptional control. Gene expression is regulated primarily by transcriptional regulators that bind to cis-acting DNA sequences, also called regulatory elements. The pattern of expression for a particular gene is the result of the sum of the activities of the various transcriptional regulators that act on that gene. Therefore, genes that have a similar set of regulatory elements will also have a similar expression pattern and will tend to cluster together. Of course, it is also possible, and quite common, for genes that have different regulatory elements to be expressed coordinately under certain circumstances.

It is anticipated that the analysis of more than one gene cluster will be useful not only for diagnosing transplant rejection but also for determining appropriate medical interventions. For example, chronic allograft nephropathy is a general description for a disorder that has many variations and many different optimal treatment strategies. In one embodiment, the invention provides a method for simultaneously identifying graft rejection and determining an appropriate treatment. In general, the invention provides methods comprising measuring representatives of different, informative biomarker genes which can represent gene clusters, that indicate an appropriate treatment protocol.

Detecting Gene Expression

In certain aspects of the present invention, the magnitude of expression is determined for one or more biomarker genes in sample obtained from a subject. The sample can comprise cells obtained from the subject, such as from a graft biopsy. Other samples include, but are not limited to fluid samples such as blood, plasma, serum, lymph, CSF, cystic fluid, ascites, urine, stool and bile. The sample may also be obtained from bronchoalveolar lavage fluid, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft.

Many different methods are known in the art for measuring gene expression. Classical methods include quantitative RT-PCR, Northern blots and ribonuclease protection assays. Certain examples described herein use competitive reverse transcription (RT)-PCR to measure the magnitude of expression of biomarker genes. Such methods may be used to examine expression of subject genes as well as entire gene clusters. However, as the number of genes to be examined increases, the time and expense may become cumbersome.

Large scale detection methods allow faster, less expensive analysis of the expression levels of many genes simultaneously. Such methods typically involve an ordered array of probes affixed to a solid substrate. Each probe is capable of hybridizing to a different set of nucleic acids. In one method, probes are generated by amplifying or synthesizing a substantial portion of the coding regions of various genes of interest. These genes are then spotted onto a solid support. Then, mRNA samples are obtained, converted to cDNA, amplified and labeled (usually with a fluorescence label). The labeled cDNAs are then applied to the array, and cDNAs hybridize to their respective probes in a manner that is linearly related to their concentration. Detection of the label allows measurement of the amount of each cDNA adhered to the array.

Many methods for performing such DNA array experiments are well known in the art. Exemplary methods are described below but are not intended to be limiting.

Microarrays are known in the art and consist of a surface to which probes that correspond in sequence to gene products (e.g., cDNAs, mRNAs, oligonucleotides) are bound at known positions. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid derivative to which a particular cognate cDNA can specifically hybridize. The nucleic acid or derivative of the binding site can be, e.g., a synthetic oligomer, a full-length cDNA, a less-than full length cDNA, or a gene fragment.

Usually the microarray will have binding sites corresponding to at least 100 genes and more preferably, 500, 1000, 4000 or more. In certain embodiments, the most preferred arrays will have about 98-100% of the genes of a particular organism represented. In other embodiments, customized microarrays that have binding sites corresponding to fewer, specifically selected genes can be used. In certain embodiments, customized microarrays comprise binding sites for fewer than 4000, fewer than 1000, fewer than 200 or fewer than 50 genes, and comprise binding sites for at least 2, preferably at least 3, 4, 5 or more genes of any of the biomarkers of Table 2. Preferably, the microarray has binding sites for genes relevant to testing and confirming a biological network model of interest.

The nucleic acids to be contacted with the microarray may be prepared in a variety of ways. Methods for preparing total and poly(A)+ RNA are well known and are described generally in Sambrook et al., supra. Labeled cDNA is prepared from mRNA by oligo dT-primed or random-primed reverse transcription, both of which are well known in the art (see e.g., Klug and Berger, 1987, Methods Enzymol. 152:316-325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Nature Biotech. 14:1675). The cDNAs or RNAs can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescent labels are used, many suitable fluorophores are known, including fluorescein, lissamine, phycoerythrin, rhodamine (Perkin Elmer Cetus), Cy2, Cy3, Cy3.5, Cy5, Cy5.5, Cy7, Fluor X (Amersham) and others (see, e.g., Kricka, 1992, Academic Press San Diego, Calif.).

In another embodiment, a label other than a fluorescent label is used. For example, a radioactive label, or a pair of radioactive labels with distinct emission spectra, can be used (see Zhao et al., 1995, Gene 156:207; Pietu et al., 1996, Genome Res. 6:492). However, use of radioisotopes is a less-preferred embodiment.

Nucleic acid hybridization and wash conditions are chosen so that the population of labeled nucleic acids will specifically hybridize to appropriate, complementary nucleic acids affixed to the matrix. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch.

Optimal hybridization conditions will depend on the length (e.g., oligomer versus polynucleotide greater than 200 bases) and type (e.g., RNA, DNA, PNA) of labeled nucleic acids and immobilized polynucleotide or oligonucleotide. General parameters for specific (i.e., stringent) hybridization conditions for nucleic acids are described in Sambrook et al, supra, and in Ausubel et al., 1987, Current Protocols in Molecular Biology, Greene Publishing and Wiley-Interscience, New York, which is incorporated in its entirety for all purposes. Non-specific binding of the labeled nucleic acids to the array can be decreased by treating the array with a large quantity of non-specific DNA—a so-called "blocking" step.

When fluorescently labeled probes are used, the fluorescence emissions at each site of a transcript array can be, preferably, detected by scanning confocal laser microscopy. When two fluorophores are used, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Research 6:639-645). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, Genome Res. 6:639-645 and in other references cited herein. Alternatively, the fiber-optic bundle described by Ferguson et al., 1996, Nature Biotech. 14:1681-1684, may be used to monitor mRNA abundance levels at a large number of sites simultaneously. Fluorescent microarray scanners are commercially available from Affymetrix, Packard BioChip Technologies, BioRobotics and many other suppliers.

Signals are recorded, quantitated and analyzed using a variety of computer software. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores is preferably calculated. The ratio is independent of the absolute expression level of the cognate gene, but is useful for genes whose expression is significantly modulated by drug administration, gene deletion, or any other tested event.

In one embodiment, transcript arrays reflecting the transcriptional state of a cell of interest are made by hybridizing a mixture of two differently labeled sets of cDNAs to the microarray. One cell is a cell of interest while the other is used as a standardizing control. The relative hybridization of each cell's cDNA to the microarray then reflects the relative expression of each gene in the two cells.

The expression levels of biomarkers in different samples and conditions may be compared using a variety of statistical methods. A variety of statistical methods are available to assess the degree of relatedness in expression patterns of different genes. The statistical methods may be broken into two related portions: metrics for determining the relatedness of the expression pattern of one or more gene, and clustering methods, for organizing and classifying expression data based on a suitable metric (Sherlock, 2000, Curr. Opin. Immunol. 12:201-205; Butte et al., 2000, Pacific Symposium on Biocomputing, Hawaii, World Scientific, p. 418-29).

In one embodiment, supervised learning methods are used such as PLS and other supervised learning algorithms such as neural networks (NN), support vector machine (SVP, or k-nearest neighbors (KNN) may be used as a means of predictive modeling. As detailed in Example I, the biomarkers of the invention are useful as descriptors in a PLS model to classify tissue with CAN (e.g., selected grades of CAN).

In another embodiment, non-supervised methods are used such as Pearson correlation, Euclidean distance measurements, entropic calculations (Butte et al. 2000, supra), agglomerative clustering methods, divisive clustering methods and self-organizing maps (SOM).

In another aspect, the invention provides probe sets. Preferred probe sets are designed to detect expression of one or more genes and provide information about the status of a graft. Preferred probe sets of the invention comprise probes that are useful for the detection of at least two genes belonging to any of the biomarker genes of Table 2. Probe sets of the invention comprise probes useful for the detection of no more than 10,000 gene transcripts, and preferred probe sets will comprise probes useful for the detection of fewer than 4000, fewer than 1000, fewer than 200, fewer than 100, fewer than 90, fewer than 80, fewer than 70, fewer than 60, fewer than 50, fewer than 40, fewer than 30, fewer than 20, fewer than 10 gene transcripts. The probe sets of the invention are targeted at the detection of gene transcripts that are informative about transplant status. Probe sets of the invention may also comprise a large or small number of probes that detect gene transcripts that are not informative about transplant status. In preferred embodiments, probe sets of the invention are affixed to a solid substrate to form an array of probes. It is anticipated that probe sets may also be useful for multiplex PCR. The probes of probe sets may be nucleic acids (e.g., DNA, RNA, chemically modified forms of DNA and RNA), or PNA, or any other polymeric compound capable of specifically interacting with the desired nucleic acid sequences.

Computer readable media comprising a biomarker(s) of the present invention is also provided. As used herein, "computer readable media" includes a medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a biomarker of the present invention.

As used herein, "recorded" includes a process for storing information on computer readable medium. Those skilled in the art can readily adopt any of the presently known methods for recording information on computer readable medium to generate manufactures comprising the biomarkers of the present invention.

A variety of data processor programs and formats can be used to store the biomarker information of the present invention on computer readable medium. For example, the nucleic acid sequence corresponding to the biomarkers can be represented in a word processing text file, formatted in commercially-available software such as WordPerfect and MicroSoft Word, or represented in the form of an ASCII file, stored in a database application, such as DB2, Sybase, Oracle, or the like. Any number of dataprocessor structuring formats (e.g., text file or database) may be adapted in order to obtain computer readable medium having recorded thereon the biomarkers of the present invention.

By providing the biomarkers of the invention in computer readable form, one can routinely access the biomarker sequence information for a variety of purposes. For example, one skilled in the art can use the nucleotide or amino acid sequences of the invention in computer-readable form to compare a target sequence or target structural motif with the sequence information stored within the data storage means. Search means are used to identify fragments or regions of the sequences of the invention which match a particular target sequence or target motif.

The invention also includes an array comprising a biomarker(s) of the present invention. The array can be used to assay expression of one or more genes in the array. In one embodiment, the array can be used to assay gene expression in a tissue to ascertain tissue specificity of genes in the array. In this manner, up to about 8600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development and differentiation, disease progression, in vitro processes, such a cellular transformation and senescence, autonomic neural and neurological processes, such as, for example, pain and appetite, and cognitive functions, such as learning or memory. The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and diseased cells. This provides a battery of genes that could serve as a molecular target for diagnosis or therapeutic intervention.

Proteins

It is further anticipated that increased levels of certain proteins may also provide diagnostic information about transplants. In certain embodiments, one or more proteins encoded by genes of Table 2 may be detected, and elevated or decreased protein levels may be used to diagnose graft rejection. In a preferred embodiment, protein levels are detected in a post-transplant fluid sample, and in a particularly preferred embodiment, the fluid sample is peripheral blood or urine. In another preferred embodiment, protein levels are detected in a graft biopsy.

In view of this specification, methods for detecting proteins are well known in the art. Examples of such methods include Western blotting, enzyme-linked immunosorbent assays (ELISAs), one- and two-dimensional electrophoresis, mass spectroscopy and detection of enzymatic activity. Suitable antibodies may include polyclonal, monoclonal, fragments (such as Fab fragments), single chain antibodies and other forms of specific binding molecules.

Predictive Medicine

The present invention pertains to the field of predictive medicine in which diagnostic assays, prognostic assays, pharmacogenetics and monitoring clinical trials are used for prognostic (predictive) purposes to thereby diagnose and treat a subject prophylactically. Accordingly, one aspect of the present invention relates to diagnostic assays for determining biomarker protein and/or nucleic acid expression from a sample (e.g., blood, serum, cells, tissue) to thereby determine whether a subject is likely to reject a transplant.

Another aspect of the invention pertains to monitoring the influence of agents (e.g., drugs, compounds) on the expression or activity of biomarker in clinical trials as described in further detail in the following sections.

An exemplary method for detecting the presence or absence of biomarker protein or genes of the invention in a sample involves obtaining a sample from a test subject and contacting the sample with a compound or an agent capable of detecting the protein or nucleic acid (e.g., mRNA, genomic DNA) that encodes the biomarker protein such that the presence of the biomarker protein or nucleic acid is detected in the sample. A preferred agent for detecting mRNA or genomic DNA corresponding to a biomarker gene or protein of the invention is a labeled nucleic acid probe capable of hybridizing to a mRNA or genomic DNA of the invention. Suitable probes for use in the diagnostic assays of the invention are described herein.

A preferred agent for detecting biomarker protein is an antibody capable of binding to biomarker protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "sample" is intended to include tissues, cells and biological fluids isolated from a subject, as well as tissues, cells and fluids present within a subject. That is, the detection method of the invention can be used to detect biomarker mRNA, protein, or genomic DNA in a sample in vitro as well as in vivo. For example, in vitro techniques for detection of biomarker mRNA include Northern hybridizations and in situ hybridizations. In vitro techniques for detection of biomarker protein include enzyme linked immunosorbent assays (ELISAs), Western blots, immunoprecipitations and immunofluorescence. In vitro techniques for detection of biomarker genomic DNA include Southern hybridizations. Furthermore, in vivo techniques for detection of biomarker protein include introducing, into a subject, a labeled anti-biomarker antibody. For example, the antibody can be labeled with a radioactive biomarker whose presence and location in a subject can be detected by standard imaging techniques.

In one embodiment, the sample contains protein molecules from the test subject. Alternatively, the sample can contain mRNA molecules from the test subject or genomic DNA molecules from the test subject. A preferred sample is a serum sample isolated by conventional means from a subject.

The methods further involve obtaining a control sample (e.g., biopsies from non transplanted healthy kidney or from transplanted healthy kidney showing no sign of rejection) from a control subject, contacting the control sample with a compound or agent capable of detecting biomarker protein, mRNA, or genomic DNA, such that the presence of biomarker protein, mRNA or genomic DNA is detected in the sample, and comparing the presence of biomarker protein, mRNA or genomic DNA in the control sample with the presence of biomarker protein, mRNA or genomic DNA in the test sample.

The invention also encompasses kits for detecting the presence of biomarker in a sample. For example, the kit can comprise a labeled compound or agent capable of detecting biomarker protein or mRNA in a sample; means for determining the amount of biomarker in the sample; and means for comparing the amount of biomarker in the sample with a standard. The compound or agent can be packaged in a suitable container. The kit can further comprise instructions for using the kit to detect biomarker protein or nucleic acid.

The diagnostic methods described herein can furthermore be utilized to identify subjects having or at risk of developing a disease or disorder associated with aberrant biomarker expression or activity. As used herein, the term "aberrant" includes a biomarker expression or activity which deviates from the wild type biomarker expression or activity. Aberrant expression or activity includes increased or decreased expression or activity, as well as expression or activity which does not follow the wild type developmental pattern of expression or the subcellular pattern of expression. For example, aberrant biomarker expression or activity is intended to include the cases in which a mutation in the biomarker gene causes the biomarker gene to be under-expressed or over-expressed and situations in which such mutations result in a non-functional biomarker protein or a protein which does not function in a wild-type fashion, e.g., a protein which does not interact with a biomarker ligand or one which interacts with a non-biomarker protein ligand.

Furthermore, the prognostic assays described herein can be used to determine whether a subject can be administered an agent (e.g., an agonist, antagonist, peptidomimetic, protein, peptide, nucleic acid, small molecule, or other drug candidate) to reduce the risk of rejection, e.g., cyclospsorin. Thus, the present invention provides methods for determining whether a subject can be effectively treated with an agent for a disorder associated with increased gene expression or activity of the combination of genes in Table 2.

Monitoring the influence of agents (e.g., drugs) on the expression or activity of a genes can be applied not only in basic drug screening, but also in clinical trials. For example, the effectiveness of an agent determined by a screening assay as described herein to increase gene expression, protein levels, or up-regulate activity, can be monitored in clinical trials of subjects exhibiting by examining the molecular signature and any changes in the molecular signature during treatment with an agent.

For example, and not by way of limitation, genes and their encoded proteins that are modulated in cells by treatment with an agent (e.g., compound, drug or small molecule) which modulates gene activity can be identified. In a clinical trial, cells can be isolated and RNA prepared and analyzed for the levels of expression of genes implicated associated with rejection. The levels of gene expression (e.g., a gene expression pattern) can be quantified by northern blot analysis or RT-PCR, as described herein, or alternatively by measuring the amount of protein produced, by one of the methods as described herein. In this way, the gene expression pattern can serve as a molecular signature, indicative of the physiological response of the cells to the agent. Accordingly, this response state may be determined before, and at various points during treatment of the subject with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a gene or combination of genes, the protein encoded by the genes, mRNA, or genomic DNA in the preadministration sample; (iii) obtaining one or more post-administration samples from the subject; (iv) detecting the level of expression or activity of the biomarker protein, mRNA, or genomic DNA in the post-administration samples; (v) comparing the level of expression or activity of the biomarker protein, mRNA, or genomic DNA in the pre-administration sample with the a gene or combination of genes, the protein encoded by the genes, mRNA, or genomic DNA in the post administration sample or samples; and (vi) altering the administration of the agent to the subject accordingly. For example, increased administration of the agent may be desirable to decrease the expression or activity of the genes to lower levels, i.e., to increase the effectiveness of the agent to protect against transplant rejection. Alternatively, decreased administration of the agent may be desirable to decrease expression or activity of biomarker to lower levels than detected, i.e., to decrease the effectiveness of the agent e.g., to avoid toxicity. According to such an embodiment, gene expression or activity may be used as an indicator of the effectiveness of an agent, even in the absence of an observable phenotypic response.

The present invention provides for both prophylactic and therapeutic methods for preventing transplant rejection. With regards to both prophylactic and therapeutic methods of treatment, such treatments may be specifically tailored or modified, based on knowledge obtained from the field of pharmacogenomics. "Pharmacogenomics", as used herein, includes the application of genomics technologies such as gene sequencing, statistical genetics, and gene expression analysis to drugs in clinical development and on the market. More specifically, the term refers the study of how a subject's genes determine his or her response to a drug (e.g., a subject's "drug response phenotype", or "drug response genotype"). Thus, another aspect of the invention provides methods for tailoring a subject's prophylactic or therapeutic treatment with either the biomarker molecules of the present invention or biomarker modulators according to that subject's drug response genotype. Pharmacogenomics allows a clinician or physician to target prophylactic or therapeutic treatments to subjects who will most benefit from the treatment and to avoid treatment of subjects who will experience toxic drug-related side effects.

In one aspect, the invention provides a method for preventing transplant rejection in a subject, associated with increased biomarker expression or activity, by administering to the subject a compound or agent which modulates biomarker expression. Examples of such compounds or agents are e.g., compounds or agents having immunosuppressive properties, such as those used in transplantation (e.g., a calcineurin inhibitor, cyclosporin A or FK 506); a mTOR inhibitor (e.g., rapamycin, 40-O-(2-hydroxyethyl)-rapamycin, CCI779, ABT578, AP23573, biolimus-7 or biolimus-9); an ascomycin having immuno-suppressive properties (e.g., ABT-281, ASM981, etc.); corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor (e.g., as disclosed in WO 02/38561 or WO 03/82859, the compound of Example 56 or 70); a JAK3 kinase inhibitor (e.g., N-benzyl-3,4-dihydroxy-benzylidene-cyanoacetamide a-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)- amino]-piperidin-1-yl}-3-oxo-propionitrile, in free form or in a pharmaceutically acceptable salt form, e.g., mono-citrate (also called CP-690,550), or a compound as disclosed in WO 04/052359 or WO 05/066156); a SIP receptor agonist or modulator (e.g., FTY720 optionally phosphorylated or an analog thereof, e.g., 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts); immunosuppressive monoclonal antibodies (e.g., monoclonal antibodies to leukocyte receptors, e.g., MHC, CD2, CD3, CD4, CD7, CD8, CD25, CD28, CD40, CD45, CD52, CD58, CD80, CD86 or their ligands); other immunomodulatory compounds (e.g., a recombinant binding molecule having at least a portion of the extracellular domain of CTLA4 or a mutant thereof, e.g., an at least extracellular portion of CTLA4 or a mutant thereof joined to a non-CTLA4 protein sequence, e.g., CTLA4Ig (for ex. designated ATCC 68629) or a mutant thereof, e.g., LEA29Y); adhesion molecule inhibitors (e.g., LFA-1 antagonists, ICAM-1 or -3 antagonists, VCAM-4 antagonists or VLA-4 antagonists). These compounds or agents may also be used in combination.

Another aspect of the invention pertains to methods of modulating biomarker protein expression or activity for therapeutic purposes. Accordingly, in an exemplary embodiment, the modulatory method of the invention involves contacting a cell with a biomarker protein or agent that modulates one or more of the activities of a biomarker protein activity associated with the cell. An agent that modulates biomarker protein activity can be an agent as described herein, such as a nucleic acid or a protein, a naturally-occurring target molecule of a biomarker protein (e.g., a biomarker protein substrate), a biomarker protein antibody, a biomarker protein agonist or antagonist, a peptidomimetic of a biomarker protein agonist or antagonist, or other small molecule. In one embodiment, the agent stimulates one or more biomarker protein activities. Examples of such stimulatory agents include active biomarker protein and a nucleic acid molecule encoding biomarker protein that has been introduced into the cell. In another embodiment, the agent inhibits one or more biomarker protein activities. Examples of such inhibitory agents include antisense biomarker protein nucleic acid molecules, anti-biomarker protein antibodies, and biomarker protein inhibitors. These modulatory methods can be performed in vitro (e.g., by culturing the cell with the agent) or, alternatively, in vivo (e.g., by administering the agent to a subject). As such, the present invention provides methods of treating a subject afflicted with a disease or disorder characterized by aberrant expression or activity of a biomarker protein or nucleic acid molecule. In one embodiment, the method involves administering an agent (e.g., an agent identified by a screening assay described herein), or combination of agents that modulates (e.g., up-regulates or down-regulates) biomarker protein expression or activity. In another embodiment, the method involves administering a biomarker protein or nucleic acid molecule as therapy to compensate for reduced or aberrant biomarker protein expression or activity. Stimulation of biomarker protein activity is desirable in situations in which biomarker protein is abnormally down-regulated and/or in which increased biomarker protein activity is likely to have a beneficial effect. For example, stimulation of biomarker protein activity is desirable in situations in which a biomarker is down-regulated and/or in which increased biomarker protein activity is likely to have a beneficial effect. Likewise, inhibition of biomarker protein activity is desirable in situations in which biomarker protein is abnormally up-regulated and/or in which decreased biomarker protein activity is likely to have a beneficial effect.

The biomarker protein and nucleic acid molecules of the present invention, as well as agents, or modulators which have a stimulatory or inhibitory effect on biomarker protein activity (e.g., biomarker gene expression), as identified by a screening assay described herein, can be administered to subjects to treat (prophylactically or therapeutically) biomarker-associated disorders (e.g., prostate cancer) associated with aberrant biomarker protein activity. In conjunction with such treatment, pharmacogenomics (i.e., the study of the relationship between a subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a biomarker molecule or biomarker modulator as well as tailoring the dosage and/or therapeutic regimen of treatment with a biomarker molecule or biomarker modulator.

One pharmacogenomics approach to identifying genes that predict drug response, known as "a genome-wide association", relies primarily on a high-resolution map of the human genome consisting of already known gene-related biomarkers (e.g., a "bi-allelic" gene biomarker map which consists of 60,000-100,000 polymorphic or variable sites on the human genome, each of which has two variants). Such a high-resolution genetic map can be compared to a map of the genome of each of a statistically significant number of subjects taking part in a Phase II/III drug trial to identify biomarkers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, subjects can be grouped into genetic categories depending on a particular pattern of SNPs in their subject genome. In such a manner, treatment regimens can be tailored to groups of genetically similar subjects, taking into account traits that may be common among such genetically similar subjects.

Alternatively, a method termed the "candidate gene approach", can be utilized to identify genes that predict drug response. According to this method, if a gene that encodes a drugs target is known (e.g., a biomarker protein of the present invention), all common variants of that gene can be fairly easily identified in the population and it can be determined if having one version of the gene versus another is associated with a particular drug response.

Information generated from more than one of the above pharmacogenomics approaches can be used to determine appropriate dosage and treatment regimens for prophylactic or therapeutic treatment of a subject. This knowledge, when applied to dosing or drug selection, can avoid adverse reactions or therapeutic failure and thus enhance therapeutic or prophylactic efficiency when treating a subject with a biomarker molecule or biomarker modulator, such as a modulator identified by one of the exemplary screening assays described herein.

This invention is further illustrated by the following examples which should not be construed as limiting. The contents of all references, patents and published patent applications cited throughout this application, are incorporated herein by reference.

EXAMPLES

Example 1

Identifying Biomarkers Indicative of Chronic/Sclerosing Allograft Nephropathy

Introduction and Purpose of the Studies of the Invention

Histopathological evaluation of biopsy tissue is the gold standard of diagnosis of chronic renal allograft nephropathy (CAN), while prediction of the onset of CAN is currently impossible. Molecular diagnostics, like gene expression profiling, may aid to further refine the BANFF 97 disease classification (Racusen L C, et al., Kidney Int. 55(2):713-23 (1999)), and may also be employed as predictive or early diagnostic biomarkers when applied at early time points after transplantation when by other means graft dysfunction is not yet detectable. In the present study, gene expression profiling was applied to biopsy RNA extracted from renal protocol biopsies from renal transplant patients. Specifically, to identify genomic biomarkers of chronic/sclerosing allograft nephropathy which, based on mRNA expression levels derived from kidney biopsies of renal transplant patients, allows for detection/diagnosis of CAN.

1.1 Patient Stratification

Kidney biopsy samples from renal transplant patients of two clinical centers were used; center "A" provided in total 71 samples and center "B" provided in total 32 samples for this biomarker analysis. The sample distribution across the different grades of chronic/sclerosing allograft nephropathy (CAN) is shown below in Table 4.

TABLE 4

Number of Samples with Different Grade of CAN Recruited from Two Clinical Centers

| Grade of CAN | (A) | (B) | Total |
| --- | --- | --- | --- |
| 0: Normal | 53 | 12 | 65 |
| I: mild | 17 | 4 | 21 |
| II: moderate | 1 | 8 | 9 |
| III: severe | 0 | 8 | 8 |
| Total | 71 | 32 | 103 |

In total, 103 samples could be employed, with 65 samples exhibiting no signs of CAN, in the following referred to as "Normal" and 38 samples of different grade of CAN. Important to note, there was only 1 sample with grade II and no sample with grade III in center A.

1.2 Sample Processing

The kidney biopsy samples which were used in this study were collected from several clinical centers providing kidney biopsies from patients with symptoms of acute and chronic allograft rejection and kidney biopsy samples from transplant patients with normal renal function, i.e., no signs of acute or chronic rejections at the time of investigation.

Kidney biopsy samples are examined and judged by a pathologist of the clinical center according to the Banff 97 criteria. A copy of the pathological findings of the kidney biopsy and the demographic data, history of disease and other clinical parameters were stored in a database.

mRNA was extracted at the clinical center according as detailed below. Extracted mRNA samples were analysed for gene expression pattern by hybridization on Affymetrix U133 Plus 2 microarray. All samples from one center were analyzed in one batch. MAS5 normalized transcription levels are stored together with the clinical data in a database.

1.3 RNA Extraction and Purification

Total RNA was obtained by acid guanidinium thiocyanate-phenol-chloroform extraction (Trizol, Invitrogen Life Technologies) from each frozen tissue section and the total RNA was then purified on an affinity resin (RNeasy, Qiagen) according to the manufacturer's instructions and quantified. Total RNA was quantified by the absorbance at $\lambda=260$ nm ($A_{260nm}$), and the purity was estimated by the ratio $A_{260nm}/A_{280nm}$. Integrity of the RNA molecules was confirmed by non-denaturing agarose gel electrophoresis. RNA was stored at approximately $-80°$ C. until analysis.

1.4 GeneChip Experiment

All DNA microarray experiments were conducted in the Genomics Factory EU, Basel, Switzerland, following the instructions of the manufacturer of the GeneChip system (Affymetrix, Inc., San Diego, Calif., USA) and as previously described (Lockhart D J, et al., Nat. Biotechnol. 14(13):1675-80 (1996)).

Total RNA was obtained from snap frozen kidney biopsy samples by acid guanidinium isothiocyanate-phenol-chloroform extraction (Chomczynski P, et al., Anal Biochem 162 (1):156-9 (1987)) using Trizol (Invitrogen Life Technologies, San Diego, Calif., USA) and was purified on an affinity resin column (RNeasy; Qiagen, Hilden, Germany) according to the manufacturer's instructions. Total RNA was amplified with a T7 based polymerase protocol (Affymetrix, GeneChip® Expression 3'-Amplification Reagents Two-Cycle cDNA Synthesis Kit). Human HG_133_plus2_target arrays [Affymetrix] were used, comprising more than 54,000 probe sets, analyzing over 35,000 transcripts and variants from over 28,000 well-substantiated human genes. One GeneChip was used per kidney biopsy. The resultant image files (.dat files) were processed using the Microarray Analysis Suite 5 (MAS5) software (Affymetrix). Tab-delimited files containing data regarding signal intensity (Signal) and categorical expression level measurement (Absolute Call) were obtained. Raw data were converted to expression levels using a "target intensity" of 150. The data were checked for quality prior to uploading to an electronic database.

1.4.1 Data Analysis

Data analysis was performed using Silicon Genetics software package GeneSpring version 8.1 and with SIMCA-P+ (version 11.0) by Umetrics AB, Sweden. MAS5 transformed transcriptomic data were normalized on the median of the normal samples of each center, separately. (GeneSpring Version 8.1). Probesets showing present or marginal flags in more than 25% of all samples were included in the analysis yielding a startset of 18'149 probesets.

The information content of these data, which is a conjunction of numerical changes and biological information was evaluated by comparing the data to various databases and scientific literature. Several databases were used to explore biological relevance of the datasets, e.g., PubMed (http:// www.ncbi.nlm.nih.gov), NIH David (http://david.niaid.nih.gov), Affymetrix (https://www.affymetrix.com), as well internal databases.

1.4.2 Predictive Modelling and Validation Techniques

Normalized expression values were log-transformed and Pareto scaled. Partial Least Squares (PLS) was employed as a supervised learning algorithm.

Partial Least Squares (PLS) is one of the methods of choice when the issue is the prediction of a variable such as grade of chronic rejection and there exist a very large number of correlated predictors such as a predictor set of genes. It is, probably, one of the best statistical approaches for prediction when there is multicollineality and a much larger number of variables than observations.

The goal of PLS regression is to provide a dimension reduction strategy in a situation where one wants to relate a set of response variables Y to a set of predictor variables X. PLS identifies orthogonal X-components $t_h = Xw_h^*$ and Y-components $u_h = Yc_h$ maximising the covariance between $t_h$ and $u_h$. It is a compromise between the principal component analyses of X and Y and the canonical correlation analysis of X and Y. Note that canonical correlation analysis or multivariate regression is not directly applicable because there are many more predictors (cDNA clones) than observations. In addition, the high multicollinearity observed with microarray data causes a poor performance of the multivariate regression and of canonical analysis even if a subset of expression levels is selected. The PLS methodology, in contrast, can be applied even when there are many more predictor variables than observations, as is the case with microarray data (Pérez-Enciso1 M, et al., Human Genetics 112(5-6): 581-92 (2003)). The particular case of PLS-DA is a PLS regression where Y is a set of binary variables describing the categories of a categorical variable on X; i.e., the number dependent, or response, variables is equal to the number of categories. Alternative discrimination strategies are found in Nguyen and Rocke (Nguyen D V, et al., Bioinformatics 18:39-50 (2002)). For each response variable, $y_k$, a regression model on the X-components is written:

$$y_k = \sum_{h=1}^{m}(Xw_h^*)c_h + e = XW^*c + e,$$

where $w_h^*$ is a p dimension vector containing the weights given to each original variable in the k-th component, and $c_h$ is the regression coefficient of $y_k$ on h-th X-component variable. The algorithm developed by Wold et al. (Wold et al., The multivariate calibration problem in chemistry solved by the PLS method. In: Ruhe A, Kagstrom B (eds) Proc Conf Matrix Pencils. Springer, Heidelberg, pp 286-293 (1983)) that allows for missing values was used. A fundamental requirement for PLS to yield meaningful answers is some preliminary variable selection, also referred to as feature extraction. This was achieved by selecting the variables on the basis of the VIP (variable importance parameter) for each variable. The VIP is a popular measure in the PLS literature and is defined for variable j as:

$$VIP_j = \left\{ p \sum_{h=1}^{m} \sum_{k} R^2(y_k, t_h) w_{hj}^2 \bigg/ \sum_{h=1}^{m} \sum_{k} R^2(y_k, t_h) \right\}^{1/2},$$

(Eriksson L, et al., Umetrics, Umea (1999); (Tenenhaus M, La régression PLS. Editions Technip, Paris (1998)) for each j-th predictor variable j=1, p, where $R^2(a,b)$ stands for the squared correlation between items in vector a and b, and $t_h = X_{h-1} w_h$, where $X_{h-1}$ is the residual matrix in the regression of X on components $t_1 \ldots t_{h-1}$ and $w_h$ is a vector of norm 1 (in the PLS regression algorithm $t_h$ is build with this normalisation constraint). Note that $w_{jh}^2$ measures the contribution of each variable j to the h-th PLS component. Thus, $VIP_j$ quantifies the influence on the response of each variable summed over all components and categorical responses (for more than two categories in Y), relative to the total sum of squares of the model; this makes the VIP an intuitively appealing measure of the global effect of each cDNA clone. The VIP has also the property of $$\sum_{j=1}^{p} VIP_j^2 = p.$$

In this work, a first analysis was carried out with all 18'149 variables (cDNA levels) and the VIP was assessed for each variable. Subsequently, only variables with VIP>1.8 were selected and included in a second final analysis. We set this strict criterion because of the large number of variables (cDNA clones) initially available. The number of PLS components was selected if a new component satisfied the $Q^2$ criterion; i.e.

$$Q_h^2 = 1 - PRESS_h/RESS_{h-1} \geq 0.05,$$

where $PRESS_h$ is the predicted sum of squares of a model containing h components, and $RESS_{h-1}$ is the residual sum of squares of a model containing h-1 components. PRESS is computed by cross validation $$PRESS_h = \sum_{i=1}^{n}(y_{h-1,i} - \hat{y}_{h-1,-i})^2,$$

with $y_{h-1,i}$ being the residual of observation i when h-1 components are fitted, and is the predicted $y_i$ obtained when the i-th observation is removed. Prediction of a new observation is simply obtained as $$\hat{y}_i = \sum_{h=1}^{m}(x_i' w_h^*)c_h,$$

where $x_i$ is the vector containing the variable records for the new observation i. Model validation was carried out via response permutation. Permutation tests are part of the computer intensive procedures that have become very popular in the last years due to their flexibility and to increasing computer power (Good PI, Permutation tests: a practical guide to resampling methods for testing hypotheses. Springer, New York, (2000)). Its principle is very simple, suppose we want to test the significance of a statistic T in a given sample. The response vector (Y) is N times permutated and $T_i$, i=1, N for each of the permutation sets is calculated. The distribution of T under the null hypothesis is approximated by the set of $T_i$ values; e.g., the 5% significance threshold will be the $0.05 \times N$ largest value of all $T_i$. Here we permuted 200 times the response vector (Y) and, redoing the analysis, the values of $Q^2$ and $R^2$ were plotted, where $$Q^2 = 1 - \sum_{h=1}^{m} PRESS_h / RESS_{h-1}$$

and $R^2$ is the fraction of the total sums of squares explained by the model. $Q^2$ is a measurement of the predictive ability of the model, whereas $R^2$ is related to the model's goodness of fit. Analyses were done with SIMCA-P software Version 11.0 (Eriksson L, et al., Umetrics, Umea (1999)).

Results

Feature extraction yielded 164 probe sets that passed the above mentioned criterion of VIP>1.8. The results of the prediction model constructed by these 164 probe sets are displayed in FIG. 1 where the model predictions are plotted against the clinically observed disease status; i.e. normal and CR1-CR3.

FIG. 1 shows the grades of chronic rejection as predicted by the model versus the actual grades of chronic rejection as assessed by the pathologists. Data obtained from the two different centers (A and B) are coded by different symbols. The solid line represents the regression line, dotted lines correspond to the 96% confidence limits and the dashed lines represent the 95% prediction interval. There is a good correlation between the predicted and the actual grades of chronic rejection.

TABLE 4

Model Performance Type: PLS Observations (N) = 103, Variables (K) = 165 (X = 164, Y = 1)

| A | $R^2X$(cum) | Eigenvalues | $R^2Y$(cum) | Q2 | $Q^2$(cum) | Significance |
|---|---|---|---|---|---|---|
| 1 | 0.293 | 30.2 | 0.519 | 0.481 | 0.481 | R1 |
| 2 | 0.432 | 14.3 | 0.629 | 0.141 | 0.554 | R1 |
| 3 | 0.480 | 5.0 | 0.784 | 0.237 | 0.659 | R1 |

The model consist of three significant components (see Table 4). The predictive power of the model is $Q^2$(cum)= 0.659 based on cross-validation.

FIG. 2 displays the results of the validation by response permutation. The horizontal axes represents the similarity measure (i.e. a correlation coefficient) of the true responses compared to the randomly permutated responses. The vertical axes represents the calculated $R^2$- and $Q^2$-values obtained with the respective permutated responses. $R^2$ is the fraction of the total sums of squares explained by the model (goodness of fit of the model) and $Q^2$ is a measurement of the predictive ability of the model. The goodness of fit of this model is not too optimal; the intercept is $R^2$=0.39 and is marginally below the critical value of 0.4. However, the predictive ability of the model is excellent as indicated by an $Q^2$-intercept of −0.01.

The combination of predictor genes that form a molecular signature and enable the prediction of chronic allograft rejection are shown in Table 2.

TABLE 2

Biomarker Genes of the Invention

| Affymetrix Probeset ID | UNIGENE | Symbol | Gene Name | Raw | Normalized Values | | | |
|---|---|---|---|---|---|---|---|---|
| | | | | | normal | CR 1 | CR 2 | CR 3 |
| 230602_at | HS.146022 | ACMSD | aminocarboxymuconate semialdehyde decarboxylase | 571 | −1.08 | 1.19 | −1.38 | −2.39 |
| 205364_at | HS.444959 | ACOX2 | acyl-Coenzyme A oxidase 2, branched chain | 276 | −1.02 | 1.03 | −1.46 | −2.52 |
| 202422_s_at | HS.268785 | ACSL4 | acyl-CoA synthetase long-chain family member 4 | 1125 | −1.03 | 1.00 | 1.40 | 1.53 |
| 205745_x_at | HS.404914 | ADAM17 | a disintegrin and metalloproteinase domain 17 (tumor necrosis factor, alpha, converting enzyme) | 227 | −1.01 | −1.02 | 1.18 | 1.67 |
| 213532_at | HS.404914 | ADAM17 | a disintegrin and metalloproteinase domain 17 (tumor necrosis factor, alpha, converting enzyme) | 259 | −1.02 | −1.08 | 1.11 | 1.49 |
| 222930_s_at | HS.461532 | AGMAT | agmatine ureohydrolase (agmatinase) | 198 | −1.04 | 1.03 | −1.57 | −4.02 |
| 229229_at | HS.34494 | AGXT2 | alanine-glyoxylate aminotransferase 2 | 858 | −1.08 | 1.34 | −1.09 | −2.15 |
| 227530_at | HS.371240 | AKAP12 | A kinase (PRKA) anchor protein (gravin) 12 | 778 | 1.00 | 1.07 | 1.06 | 1.99 |
| 218487_at | HS.1227 | ALAD | aminolevulinate, delta-, dehydratase | 499 | −1.03 | 1.02 | −1.58 | −2.42 |
| 211298_s_at | | ALB | albumin | 444 | 1.07 | 1.91 | −4.01 | −9.43 |
| 208950_s_at | HS.483239 | ALDH7A1 | aldehyde dehydrogenase 7 family, member A1 | 838 | −1.02 | −1.01 | −1.37 | −1.72 |
| 208951_at | HS.483239 | ALDH7A1 | aldehyde dehydrogenase 7 family, member A1 | 438 | −1.01 | −1.01 | −1.62 | −2.19 |
| 220148_at | HS.486520 | ALDH8A1 | aldehyde dehydrogenase 8 family, member A1 | 1505 | −1.20 | 1.32 | −1.14 | −1.85 |
| 201612_at | HS.2533 | ALDH9A1 | aldehyde dehydrogenase 9 family, member A1 | 3300 | 1.01 | −1.07 | −1.22 | −1.55 |

TABLE 2-continued

Biomarker Genes of the Invention

| Affymetrix Probeset ID | UNIGENE | Symbol | Gene Name | Raw | Normalized Values | | | |
|---|---|---|---|---|---|---|---|---|
| | | | | | normal | CR 1 | CR 2 | CR 3 |
| 205682_x_at | HS.534468 | APOM | apolipoprotein M | 633 | −1.05 | −1.08 | −1.84 | −3.82 |
| 205673_s_at | HS.19404 | ASB9 | ankyrin repeat and SOCS box-containing 9 | 131 | −1.03 | 1.06 | −1.78 | −3.82 |
| 219902_at | HS.114172 | BHMT2 | betaine-homocysteine methyltransferase 2 | 1053 | −1.10 | 1.04 | −1.40 | −2.81 |
| 204741_at | HS.505202 | BICD1 | Bicaudal D homolog 1 (*Drosophila*) | 146 | 1.02 | 1.10 | 1.67 | 1.86 |
| 223824_at | HS.149849 | C10ORF59 | chromosome 10 open reading frame 59 | 345 | −1.02 | −1.13 | −1.30 | −1.70 |
| 225687_at | HS.472716 | C20ORF129 | chromosome 20 open reading frame 129 | 107 | 1.04 | −1.05 | −1.65 | −2.32 |
| 228560_at | HS.476358 | CACNA1D | calcium channel, voltage-dependent, L type, alpha 1D | 418 | −1.13 | 1.31 | −1.11 | −1.49 |
| 216903_s_at | HS.524367 | CBARA1 | calcium binding atopy-related autoantigen 1 | 365 | −1.03 | −1.05 | −1.39 | −1.96 |
| 224027_at | HS.334633 | CCL28 | chemokine (C-C motif) ligand 28 | 27 | −1.09 | −1.09 | 1.53 | 2.35 |
| 1559590_at | HS.126688 | CHDH | choline dehydrogenase | 35 | −1.36 | 1.20 | 1.09 | −1.64 |
| 218252_at | HS.444028 | CKAP2 | cytoskeleton associated protein 2 | 190 | −1.00 | −1.27 | −1.25 | −1.46 |
| 212091_s_at | HS.474053 | COL6A1 | collagen, type VI, alpha 1 | 58 | −1.17 | −1.17 | −2.25 | −1.71 |
| 208146_s_at | HS.233389 | CPVL | carboxypeptidase, vitellogenic-like | 951 | 1.01 | −1.04 | 1.20 | 1.58 |
| 203915_at | HS.77367 | CXCL9 | chemokine (C—X—C motif) ligand 9 | 831 | 1.14 | −1.05 | −1.11 | −2.43 |
| 206878_at | HS.113227 | DAO | D-amino-acid oxidase | 202 | −1.04 | 1.11 | −1.93 | −4.55 |
| 230175_s_at | HS.203691 | DCBLD2 | discoidin, CUB and LCCL domain containing 2 | 364 | 1.01 | −1.06 | 1.11 | 1.34 |
| 217973_at | HS.9857 | DCXR | dicarbonyl/L-xylulose reductase | 907 | −1.11 | −1.30 | −1.47 | −3.56 |
| 204977_at | HS.525115 | DDX10 | DEAD (Asp-Glu-Ala-Asp) box polypeptide 10 | 343 | 1.03 | 1.02 | −1.47 | −1.97 |
| 232381_s_at | HS.520106 HS.212360 | DNAH5 | dynein, axonemal, heavy polypeptide 5 | 147 | 1.05 | 1.28 | 2.65 | 1.97 |
| 226281_at | HS.234074 | DNER | delta-notch-like EGF repeat-containing transmembrane | 484 | −1.13 | −1.07 | 1.58 | 1.49 |
| 203716_s_at | HS.368912 | DPP4 | dipeptidylpeptidase 4 (CD26, adenosine deaminase complexing protein 2) | 121 | −1.05 | 1.20 | −1.56 | −2.31 |
| 219298_at | HS.22242 | ECHDC3 | enoyl Coenzyme A hydratase domain containing 3 | 473 | −1.04 | −1.05 | −1.39 | −2.33 |
| 224189_x_at | HS.502306 | EHF | ets homologous factor | 24 | −1.14 | 1.19 | 2.14 | 1.95 |
| 209368_at | HS.212088 | EPHX2 | epoxide hydrolase 2, cytoplasmic | 334 | −1.17 | −1.26 | −1.50 | −2.64 |
| 211398_at | HS.533683 | FGFR2 | fibroblast growth factor receptor 2 | 21 | −1.04 | −1.05 | −1.84 | −2.46 |
| 211399_at | HS.533683 | FGFR2 | fibroblast growth factor receptor 3 | 27 | −1.15 | 1.09 | −1.51 | −2.87 |
| 211400_at | HS.533683 | FGFR2 | fibroblast growth factor receptor 4 | 16 | −1.46 | −1.28 | −1.43 | −2.01 |
| 230842_at | HS.533683 | FGFR2 | fibroblast growth factor receptor 5 | 11 | 1.12 | 1.06 | −2.66 | −2.18 |
| 219118_at | HS.438695 | FKBP11 | FK506 binding protein 11, 19 kDa | 85 | 1.00 | −1.00 | 1.96 | 2.19 |
| 1559011_at | HS.462392 | FLJ13773 | hypothetical protein FLJ13773 | 25 | −1.21 | 1.12 | 1.79 | 1.86 |
| 227417_at | HS.369042 | FLJ20605 | hypothetical protein FLJ20605 | 803 | −1.04 | 1.05 | −1.47 | −2.22 |
| 228397_at | HS.158783 | FLJ20618 | hypothetical protein FLJ20618 | 254 | −1.02 | 1.01 | 1.46 | 2.21 |
| 221925_s_at | HS.370147 | FLJ22490 | hypothetical protein FLJ22490 | 51 | −1.01 | 1.01 | −1.34 | −1.45 |
| 238593_at | HS.292088 | FLJ22531 | hypothetical protein FLJ22531 | 402 | −1.12 | 1.39 | 1.64 | 1.86 |
| 207876_s_at | HS.58414 | FLNC | filamin C, gamma (actin binding protein 280) | 495 | 1.49 | 1.20 | 1.14 | 1.98 |
| 215062_at | HS.149566 | FMNL2 | formin-like 2 | 65 | −1.04 | 1.38 | 1.51 | 1.82 |
| 206263_at | HS.386502 | FMO4 | flavin containing monooxygenase 4 | 388 | −1.09 | −1.11 | −1.59 | −3.50 |
| 1568955_at | | FNBP2 | LOC391156 | 358 | −1.04 | −1.14 | 1.21 | 2.35 |
| 226962_at | HS.529439 | FRBZ1 | FRBZ1 protein | 574 | 1.00 | 1.13 | 1.18 | 1.45 |
| 214093_s_at | HS.269099 | FUBP1 | far upstream element (FUSE) binding protein 1 | 277 | −1.04 | −1.02 | 1.19 | 2.00 |
| 216010_x_at | HS.169238 | FUT3 | fucosyltransferase 3 (galactoside 3(4)-L-fucosyltransferase, Lewis blood group included) | 32 | −1.24 | −1.33 | −1.52 | −2.66 |
| 228238_at | HS.531856 | GAS5 | growth arrest-specific 5 | 260 | 1.01 | 1.07 | 1.25 | 1.83 |
| 213133_s_at | HS.435741 HS.546256 | GCSH | glycine cleavage system protein H (aminomethyl carrier) | 443 | −1.01 | −1.14 | −1.42 | −1.85 |
| 230025_at | HS.444663 | GJC1 | gap junction protein, chi 1, 31.9 kDa (connexin 31.9) | 102 | 1.01 | −1.13 | −1.24 | −1.52 |
| 202382_s_at | HS.278500 | GNPDA1 | glucosamine-6-phosphate deaminase 1 | 690 | −1.03 | −1.06 | −1.30 | −2.10 |
| 224997_x_at | HS.533566 | H19 | H19, imprinted maternally expressed untranslated mRNA | 336 | 1.28 | 1.10 | −1.04 | 1.48 |
| 205012_s_at | HS.157394 HS.513265 | HAGH | hydroxyacylglutathione hydrolase | 455 | −1.06 | −1.13 | −1.56 | −2.26 |
| 226137_at | HS.77558 HS.546885 | HMGN3 | high mobility group nucleosomal binding domain 3 | 559 | 1.01 | −1.03 | 1.20 | 1.88 |
| 204934_s_at | HS.182385 | HPN | hepsin (transmembrane protease, serine 1) | 436 | −1.20 | −1.04 | −1.25 | −2.06 |
| 210253_at | HS.90753 | HTATIP2 | HIV-1 Tat interactive protein 2, 30 kDa | 231 | −1.04 | 1.00 | 1.28 | 1.39 |

TABLE 2-continued

Biomarker Genes of the Invention

| Affymetrix Probeset ID | UNIGENE | Symbol | Gene Name | Raw | Normalized Values | | | |
|---|---|---|---|---|---|---|---|---|
| | | | | | normal | CR 1 | CR 2 | CR 3 |
| 235549_at | HS.148741 | IBRDC2 | IBR domain containing 2 | 28 | −1.36 | 1.03 | 1.31 | 2.04 |
| 202410_x_at | HS.373908 HS.523414 | IGF2 | insulin-like growth factor 2 (somatomedin A) | 10 | 1.04 | 1.09 | −1.37 | −1.32 |
| 210881_s_at | HS.373908 HS.523414 | IGF2 | insulin-like growth factor 2 (somatomedin A) | 7 | 1.18 | 1.06 | −1.20 | 1.03 |
| 1553594_a_at | HS.37062 HS.515247 | INSL3, JAK3 | Janus kinase 3 (a protein tyrosine kinase, leukocyte) | 108 | −1.07 | −1.26 | −1.30 | −1.68 |
| 210840_s_at | HS.430551 | IQGAP1 | IQ motif containing GTPase activating protein 1 | 566 | 1.05 | −1.10 | 1.39 | 1.71 |
| 203752_s_at | HS.2780 | JUND | jun D proto-oncogene | 1456 | −1.00 | 1.02 | 1.09 | 1.36 |
| 211806_s_at | HS.411299 | KCNJ15 | potassium inwardly-rectifying channel, subfamily J, member 15 | 303 | −1.03 | −1.12 | −1.44 | −1.82 |
| 238428_at | HS.411299 | KCNJ15 | potassium inwardly-rectifying channel, subfamily J, member 15 | 211 | −1.04 | 1.04 | −1.45 | −1.64 |
| 220116_at | HS.98280 | KCNN2 | potassium intermediate/small conductance calcium-activated channel, subfamily N, member 2 | 60 | −1.10 | −1.05 | −2.39 | −3.45 |
| 215268_at | HS.472475 | KIAA0754 | KIAA0754 protein | 88 | −1.03 | 1.18 | 1.97 | 1.94 |
| 213913_s_at | HS.192492 | KIAA0984 | KIAA0984 protein | 125 | −1.02 | 1.05 | 1.26 | 1.69 |
| 244370_at | HS.124128 | KIAA2022 | KIAA2022 protein | 188 | −1.10 | −1.03 | 1.37 | 1.52 |
| 202962_at | HS.444767 | KIF13B | kinesin family member 13B | 598 | −1.08 | 1.03 | −1.06 | −1.56 |
| 216568_x_at | HS.533782 | KRT8 | keratin 8 | 24 | −1.12 | −1.06 | 1.66 | 2.51 |
| 242424_at | HS.370457 | LETMD1 | LETM1 domain containing 1 | 51 | −1.18 | 1.46 | 2.70 | 2.40 |
| 227285_at | HS.54680 | LOC148523 | hypothetical protein BC017397 | 194 | −1.07 | −1.34 | −1.68 | −2.34 |
| 228857_at | HS.537654 | LOC285831 | hypothetical protein LOC285831 | 152 | 1.01 | 1.06 | −1.25 | −1.32 |
| 230554_at | HS.298252 | LOC348158 | hypothetical protein LOC123876 | 4581 | −1.25 | 1.38 | −1.07 | −1.58 |
| 231001_at | HS.32478 | LOC387758 | similar to RIKEN cDNA 1110018M03 | 214 | 1.01 | 1.15 | 1.57 | 2.06 |
| 227372_s_at | HS.489237 | LOC55971 | insulin receptor tyrosine kinase substrate | 211 | −1.05 | −1.04 | 1.33 | 1.42 |
| 230931_at | HS.439074 HS.449164 | LPAL2 | lipoprotein, Lp(a)-like 2 | 271 | −1.02 | 1.34 | −1.52 | −6.27 |
| 230863_at | HS.470538 | LRP2 | low density lipoprotein-related protein 2 | 1433 | −1.21 | 1.34 | −1.15 | −1.46 |
| 243170_at | HS.543294 | LRRC2 | leucine rich repeat containing 2 | 101 | −1.04 | 1.02 | −1.30 | −1.38 |
| 236322_at | HS.197043 | MAN1C1 | mannosidase, alpha, class 1C, member 1 | 112 | −1.04 | 1.20 | 1.68 | 2.07 |
| 203929_s_at | HS.546914 HS.101174 | MAPT | microtubule-associated protein tau | 235 | 1.01 | 1.08 | −1.15 | −1.87 |
| 213333_at | HS.520967 | MDH2 | malate dehydrogenase 2, NAD (mitochondrial) | 347 | 1.01 | −1.14 | −1.22 | −1.56 |
| 1553715_s_at | HS.417710 | MGC15416 | hypothetical protein MGC15416 | 543 | −1.05 | −1.15 | −1.19 | −1.97 |
| 229596_at | HS.424907 | MGC35366 | hypothetical protein MGC35366 | 170 | −1.08 | 1.27 | −1.70 | −2.98 |
| 212462_at | HS.35758 | MYST4 | MYST histone acetyltransferase (monocytic leukemia) 4 | 323 | −1.00 | 1.06 | 1.12 | 1.42 |
| 217593_at | HS.235390 | null | hypothetical protein FLJ12895 | 143 | −1.08 | 1.16 | 1.58 | 1.87 |
| 219049_at | HS.387794 | null | chondroitin beta1,4 N-acetylgalactosaminyltransferase | 348 | −1.03 | −1.29 | 1.53 | 2.47 |
| 238469_at | HS.16512 | OGFRL1 | opioid growth factor receptor-like 1 | 48 | −1.01 | −1.13 | 1.18 | 1.70 |
| 1558017_s_at | HS.406074 | PAWR | PRKC, apoptosis, WT1, regulator | 193 | −1.05 | 1.45 | 1.58 | 1.98 |
| 213263_s_at | HS.546271 | PCBP2 | poly(rC) binding protein 2 | 383 | −1.05 | 1.02 | −1.36 | −1.82 |
| 232099_at | HS.147674 | PCDHB16 | protocadherin beta 16 | 159 | −1.01 | 1.07 | 1.54 | 2.31 |
| 205380_at | HS.143293 HS.444751 | PDZK1 | PDZ domain containing 1 | 2598 | −1.18 | 1.17 | −1.23 | −1.79 |
| 218025_s_at | HS.15250 | PECI | peroxisomal D3,D2-enoyl-CoA isomerase | 1404 | −1.09 | −1.18 | −1.47 | −2.30 |
| 202108_at | HS.36473 | PEPD | peptidase D | 1240 | −1.06 | −1.11 | −1.50 | −2.80 |
| 202464_s_at | HS.195471 | PFKFB3 | 6-phosphofructo-2-kinase/fructose-2,6-biphosphatase 3 | 2256 | −1.01 | 1.07 | 1.50 | 2.34 |
| 220944_at | HS.58356 | PGLYRP4 | peptidoglycan recognition protein 4 | 60 | −1.01 | −1.01 | −1.54 | −1.75 |
| 232530_at | HS.478230 | PLD1 | phospholipase D1, phophatidylcholine-specific | 21 | −1.16 | 1.20 | 2.66 | 4.96 |
| 232212_at | HS.334649 HS.233495 | PLEKHA8 | pleckstrin homology domain containing, family A (phosphoinositide binding specific) member 8 | 45 | −1.13 | −1.33 | −1.57 | −2.35 |
| 241916_at | HS.130759 | PLSCR1 | phospholipid scramblase 1 | 130 | −1.00 | 1.14 | 1.56 | 1.96 |
| 222653_at | HS.514278 | PNPO | pyridoxin 5'-phosphate oxidase | 370 | −1.05 | −1.12 | −1.42 | −2.01 |
| 236044_at | HS.40479 | PPAPDC1 | phosphatidic acid phosphatase type 2 domain containing 1 | 187 | 1.03 | 1.04 | −1.43 | −1.76 |
| 219195_at | HS.527078 | PPARGC1A | peroxisome proliferative activated receptor, gamma, coactivator 1, alpha | 1110 | −1.03 | 1.02 | 1.10 | 1.22 |
| 206346_at | HS.368587 | PRLR | prolactin receptor | 88 | 1.01 | 1.04 | −1.52 | −3.78 |

TABLE 2-continued

Biomarker Genes of the Invention

| Affymetrix Probeset ID | UNIGENE | Symbol | Gene Name | Raw | Normalized Values | | | |
|---|---|---|---|---|---|---|---|---|
| | | | | | normal | CR 1 | CR 2 | CR 3 |
| 204304_s_at | HS.479220 | PROM1 | prominin 1 | 1015 | −1.16 | 1.18 | 1.85 | 3.08 |
| 209123_at | HS.75438 | QDPR | quinoid dihydropteridine reductase | 855 | −1.05 | −1.10 | −1.49 | −2.84 |
| 225188_at | HS.471162 | RAPH1 | Ras association (RalGDS/AF-6) and pleckstrin homology domains 1 | 1025 | 1.01 | −1.04 | 1.27 | 1.57 |
| 235144_at | HS.129136 | RASEF | RAS and EF hand domain containing | 209 | −1.01 | 1.03 | 1.20 | 1.55 |
| 203344_s_at | HS.546282 | RBBP8 | retinoblastoma binding protein 8 | 1153 | −1.03 | −1.15 | 1.22 | 1.78 |
| 240245_at | HS.221436 | RBMS3 | RNA binding motif, single stranded interacting protein | 142 | 1.01 | 1.02 | 1.60 | 1.74 |
| 217775_s_at | HS.226007 | RDH11 | retinol dehydrogenase 11 (all-trans and 9-cis) | 573 | −1.06 | −1.21 | −1.14 | −1.68 |
| 216621_at | HS.306307 | ROCK1 | Rho-associated, coiled-coil containing protein kinase 1 | 68 | 1.02 | 1.32 | 1.50 | 1.66 |
| 206169_x_at | HS.474970 | RoXaN | rotavirus X protein associated with NSP3 | 429 | 1.03 | 1.08 | 1.37 | 1.65 |
| 225150_s_at | HS.192854 | RTKN | rhotekin | 172 | −1.10 | −1.03 | −1.37 | −2.27 |
| 229273_at | HS.135787 | SALL1 | sal-like 1 (Drosophila) | 395 | −1.10 | −1.04 | −1.03 | 1.03 |
| 205075_at | HS.159509 | SERPINF2 | serine (or cysteine) proteinase inhibitor, clade F (alpha-2 antiplasmin, pigment epithelium derived factor), member 2 | 139 | −1.12 | 1.16 | −1.02 | −1.67 |
| 214016_s_at | HS.355934 | SFPQ | splicing factor proline/glutamine rich (polypyrimidine tract binding protein associated) | 1584 | 1.02 | 1.17 | 1.60 | 2.07 |
| 213590_at | HS.369554 | SLC16A5 | solute carrier family 16 (monocarboxylic acid transporters), member 5 | 258 | −1.07 | −1.07 | 1.42 | 1.67 |
| 208177_at | HS.936 | SLC34A1 | solute carrier family 34 (sodium phosphate), member 1 | 176 | −1.05 | 1.75 | −1.41 | −4.40 |
| 238177_at | HS.481478 | SLC6A19 | solute carrier family 6 (neurotransmitter transporter), member 19 | 143 | −1.26 | 1.45 | −1.54 | −3.65 |
| 220135_s_at | HS.408567 | SLC7A9 | solute carrier family 7 (cationic amino acid transporter, y+ system), member 9 | 1017 | −1.15 | 1.36 | −1.29 | −2.76 |
| 222071_s_at | HS.127648 | SLCO4C1 | solute carrier organic anion transporter family, member 4C1 | 1060 | −1.22 | −1.01 | −1.24 | −1.38 |
| 203021_at | HS.517070 | SLPI | secretory leukocyte protease inhibitor (antileukoproteinase) | 433 | 1.03 | −1.02 | 1.67 | 2.37 |
| 233713_at | HS.66170 | SMYD2 | SET and MYND domain containing 2 | 99 | 1.04 | 1.22 | 1.27 | 2.02 |
| 210715_s_at | HS.31439 | SPINT2 | serine protease inhibitor, Kunitz type, 2 | 1265 | −1.07 | 1.03 | −1.01 | 1.10 |
| 212459_x_at | HS.186512 | SUCLG2 | succinate-CoA ligase, GDP-forming, beta subunit | 1428 | −1.02 | −1.04 | −1.24 | −1.47 |
| 227480_at | HS.131819 | SUSD2 | sushi domain containing 2 | 264 | 1.01 | 1.07 | −1.74 | −3.78 |
| 203084_at | HS.1103 | TGFB1 | transforming growth factor, beta 1 (Camurati-Engelmann disease) | 40 | −1.10 | −1.37 | −1.52 | −1.61 |
| 203085_s_at | HS.1103 | TGFB1 | transforming growth factor, beta 1 | 7 | 1.23 | 1.06 | −1.00 | 1.02 |
| 204565_at | HS.9676 | THEM2 | thioesterase superfamily member 2 | 239 | −1.07 | −1.14 | −1.75 | −2.41 |
| 212701_at | HS.511686 | TLN2 | talin 2 | 203 | −1.04 | 1.17 | −1.45 | −2.27 |
| 226860_at | HS.7337 | TMEM19 | transmembrane protein 19 | 383 | −1.04 | −1.10 | −1.37 | −1.73 |
| 200822_x_at | HS.524219 | TPI1 | triosephosphate isomerase 1 | 2029 | −1.00 | −1.19 | −1.26 | −1.44 |
| 211700_s_at | HS.434971 | TRO | trophinin | 132 | −1.12 | 1.09 | 1.80 | 2.20 |
| 208958_at | HS.154023 | TXNDC4 | thioredoxin domain containing 4 (endoplasmic reticulum) | 65 | 1.02 | 1.12 | 1.23 | 1.66 |
| 233155_at | HS.128427 | UPP2 | uridine phosphorylase 2 | 52 | −1.03 | −1.03 | −1.81 | −3.12 |
| 244622_at | HS.314338 | WDR9 | WD repeat domain 9 | 38 | −1.02 | 1.30 | 1.50 | 2.35 |
| 1555192_at | HS.489722 | ZNF277 | zinc finger protein (C2H2 type) 277 | 20 | −1.06 | −1.08 | 1.48 | 1.72 |
| 235493_at | HS.434401 | ZNF638 | zinc finger protein 638 | 156 | 1.01 | 1.17 | 1.52 | 1.38 |
| 205594_at | HS.463375 | ZNF652 | zinc finger protein 652 | 151 | 1.02 | −1.01 | 1.14 | 1.74 |
| 1569477_at | | | | 148 | 1.04 | 1.34 | 1.47 | 1.68 |
| 1569578_at | | | | 49 | −1.02 | 1.21 | 1.77 | 2.10 |
| 227955_s_at | | | | 547 | −1.02 | 1.06 | 1.44 | 1.96 |
| 230168_at | | | | 103 | −1.05 | 1.12 | 1.16 | 1.71 |
| 230332_at | | | | 260 | 1.06 | 1.20 | 1.35 | 1.58 |
| 233607_at | | | | 503 | 1.04 | 1.38 | 1.85 | 1.79 |
| 236685_at | | | | 218 | 1.05 | 1.19 | 1.33 | 1.67 |
| 237317_at | | | | 99 | 1.06 | 1.35 | 1.95 | 1.76 |
| 238299_at | | | | 90 | −1.05 | 1.12 | 1.25 | 1.66 |
| 239066_at | | | | 333 | −1.03 | 1.23 | 1.45 | 2.09 |
| 239264_at | | | | 159 | 1.06 | 1.28 | 1.57 | 1.66 |
| 239907_at | | | | 264 | −1.00 | 1.27 | 1.74 | 1.74 |
| 240800_x_at | | | | 64 | −1.06 | 1.15 | 1.32 | 1.33 |
| 242967_at | | | | 107 | −1.17 | 1.21 | −1.71 | −2.48 |

TABLE 2-continued

Biomarker Genes of the Invention

| Affymetrix Probeset ID | UNIGENE | Symbol | Gene Name | Raw | Normalized Values | | | |
|---|---|---|---|---|---|---|---|---|
| | | | | | normal | CR 1 | CR 2 | CR 3 |
| 243591_at | | | | 116 | −1.05 | 1.15 | 1.99 | 2.86 |
| 243598_at | | | | 50 | −1.09 | 1.15 | 1.71 | 1.72 |
| 244803_at | | | | 129 | −1.04 | 1.20 | 1.57 | 1.79 |

Selection of CAN-Associated Genes

A vast majority of the 164 gene probes and related genes reflect the major biological events occurring during the ongoing immune and inflammatory response observed in allograft rejection. Examples of genes include, but are not limited to a combination of genes selected from the group consisting of plasminogen, diamine oxidase, chemokine (C—X—C motif) ligand 9, Serine protease inhibitor, and kuntz type 2. Another set of genes include, but are not limited to a combination of genes selected from the group consisting of H19, SAL-like 1, Jun D proto-oncogene, fibroblast growth factor receptor 2, prolactin receptor, apolipoprotein M (APOM), and Peroxisome Proliferative Activated Receptor, gamma, coactivator 1, alpha (PPARGC1A). Another set of genes include, but are not limited to a combination of genes selected from the group consisting of kinase anchor protein 12 (AKAP12), collagen type VI (Col6A 1), 6-phosphofructo-2-kinase/fructose-2,6-biphosphatase 3 (PFKFB3), TGF-beta1, insulin-like growth factor 2, retinoblastoma binding protein 8, homeo box D13, agatine ureaohydrolase, albumin, peptidase D, microtubule associated protein Tau, thioredoxin domain containing 4 (TXNDC4), delta-Notch-like EGF repeat-containing transmembrane (DNER), connexion 31.9, dicarbonyl/L-xylulose reductase, chondroitin beta 1,4 N-acetyl-galactosaminyl-transferase (ChGn), Mal T-cell differentiation protein 2 (MAL2), Acyl-CoA Synthetase Long-chain family member 4 (ASCL4), ADAM17, Splicing Factor Proline/glutamine rich (polypyrimidine tract binding protein associated (SFPQ), Filamin C, gamma (actin binding protein 280 (FLNC), Prominin 1 (PROM1), PLSCR1, Triosephosphate Isomerase 1 (TPI1), SCCO4C1, HTATIP2, PRKC, apoptosis, WT1, regulator (PAWR). Another set of genes include, but are not limited to a combination of genes selected from the group consisting of Ataxin 7, alpha-amino-beta-carboxymuconate-epsilon-semi-aldehyde decarboxylase (ACMSD), ACOX2, ADAM17, AGXT2, ALAD, ALAS2, ALDH7A1, ASBF1, BHMT2, CCL28, CHDH, CKAP2, CPVL, DCXR, DPP4, ECHDC3, EHF, EPHX2, FKBP11, FM04, FKBP1, FUT3, GAS5, HAGH, HCCR1, HPN Hepsin, INSL3, IQGAP1, KCNJ15, KIF13B, LRP2, PDZK1, PLD1, PNPN, RTKN, SLC7A9, SLPJ, THEM2. Also within the scope of the invention are any combination of the above listed genes.

PLG: Plasminogen-Plasmin Pathway

The plasminogen-plasmin system is implicated in cell migration and matrix degradation during arterial neointima formation and atherosclerotic aneurysm formation. Plasmin proteolysis plays a major role in allograft arteriosclerosis by mediating elastin degradation, macrophage infiltration, media remodeling, medial smooth muscle cell migration, and formation of a neointima. The plasminogen-plasmin system has potential beneficial or deleterious effects in the context of renal fibrosis. Plasminogen, the key proenzyme in the plasminogen-plasmin system, does not protect mice from experimental interstitial fibrosis and may have significant pathogenetic effects. Recent studies in the biology of renal fibrosis, imply that effects of proteins such as plasminogen activator inhibitor-1 (PAI-1), tissue-type plasminogen activator (tPA), and urokinase-type plasminogen activator receptor (uPAR) on renal fibrosis occur independently from the generation of plasmin.

DAO: Diamine Oxidase-ODC Pathway

Diamine Oxidase (DAO) encodes the peroxisomal enzyme D-amino acid oxidase. The enzyme is a flavoprotein which uses flavin adenine dinucleotide (FAD) as its prosthetic group. DAO, formerly called histaminase, is found in various tissues, but is especially active in the intestinal mucosa. Its function is the oxidative deaminating of several polyamines, essential substances for cell proliferation. DAO is thus a regulating enzyme in rapidly proliferating tissues such a bone marrow and intestinal mucosa. Measuring basal as well as postheparin DAO levels has potential relevance following small bowel transplantation. Rejection of the small bowel graft leads to mucosal damage, which could conceivably lead to changes in DAO activity.

Pathway Involving CXCL9: Chemokine (C—X—C Motif) Ligand 9, MIG

Chemokines have been shown to play a critical role in leukocyte recruitment to transplanted organs and in leukocyte localisation within tissues and antagonism of certain chemokines or chemokine receptors, identified as being up-regulated during allograft rejection, it has been shown to delay leukocyte infiltration into the graft and to prolong graft survival. Expression of CXCL5 and CCL2 was found to be independent of T cell infiltration while intragraft expression of CCL3, CCL4, CCL5, CXCL9, CXCL10, XCL1 and CCL1 was clearly T cell dependent and increased significantly with time after transplantation.

Chemokine monokine induced by IFN-gamma (MIG) (CXCL9) and IFN-gamma-inducible protein 10 (IP-10) (CXCL10) are early markers of acute rejection in renal transplantation. MIG was not related to intercurrent infections or other causes for impairment of renal function. In conclusion, urinary MIG serves as a very sensitive and specific predictor for acute rejection, mirrors response to antirejection therapy, and thus may contribute to improved long-term renal allograft survival.

MIG has been implicated in bronchiolitis obliterans syndrome (BOS), characterized by a persistent peribronchiolar inflammation that eventually gives way to airway fibrosis/obliteration. Acute rejection is the main risk factor for the development of BOS and is characterized by a perivascular/bronchiolar leukocyte infiltration. The specific mechanism(s) by which these leukocytes are recruited have not been elucidated. The CXC chemokines (monokine induced by IFN-gamma (MIG)/CXC chemokine ligand (CXCL)9, IP-10/CXCL10, and IFN-inducible T cell alpha chemoattractant (ITAC)/CXCL11) act through their shared receptor, CXCR3. Because they are potent leukocyte chemoattractants and are involved in other inflammation/fibroproliferative diseases, the expression of these chemokines during an allogeneic response may promote the persistent recruitment of mononuclear cells, leading to chronic lung rejection. Elevated levels of MIG/CXCL9, IFN-inducible protein 10 (IP-10)/CXCL10, and ITAC/CXCL11 in human bronchoalveolar lavage fluid were associated with the continuum from acute to chronic rejection.

SPINT2: Serine Protease Inhibitor, Kunitz Type, 2 (HAI2), Bikunin

Bikunin is a protease inhibitor which has been shown to play a role in various processes, including inhibition of calcium oxalate crystallization, the regulation of proliferation and modulation of carcinogenesis. Bikunin appeasr to have a role in urolithiasis, proliferation and carcinogenesis. Two forms of bikunin, HAI-1 and HAI-2 appear in normal kidney and RCC cells. HAI-1 and HAI-2 were expressed in renal tubular epithelial cells. The expression of the 2 HAIs was significantly down-regulated in RCC, whereas HGFA expression was enhanced in the diseased kidney, suggesting an imbalance between HAI and its target proteinases, including HGFA, in favor of proteinase activities in RCC.

H19, Imprinted Maternally Expressed Untranslated mRNA

H19 plays an important role in the pathogenesis and growth regulatory dysfunction in cancers, e.g., breast cancer, nasopharyngeal carcinoma, chronic myeloproliferative disorders, hepatoblasotma, blasser carcinoma, kidney cancer and adrenocortical tumors.

SALL1: SAL-like 1

SALL1 enhances the canonical Wnt signaling by localizing to heterochromatin. Sall1 has an essential role in kidney development. SALL1 is a mammalian homologue of the Drosophila region-specific homeotic gene spalt (sal) and heterozygous mutations in SALL1 in humans lead to Townes-Brocks syndrome. Cells that strongly express Sall1 (Sall1-GFP(high) cells), a zinc-finger nuclear factor essential for kidney development, form colonies, and that they reconstitute a three-dimensional kidney structure in an organ culture setting.

JunD: Jun D Proto-Oncogene

JunD protects against chronic kidney disease by regulating paracrine mitogens. The AP-1 transcription factor, composed of Jun and Fos proteins, plays a crucial role in the fine tuning of cell proliferation. It has been shown that AP-1 complexes are activated during the proliferative response that parallels the development of renal lesions after nephron reduction, but little is known about the specific role of individual Jun/Fos components in the deterioration process.

FGFR2: Fibroblast Growth Factor Receptor 2

Fibroblast growth factors (FGFs) are a family of growth and differentiation factors that have been implicated in metanephric development. FGFs exert their actions through tyrosine kinase receptors, FGFRs, which are encoded by four FGFR genes (FGFR1 through FGFR4). The expression of mRNAs was detected for FGF1 through FGF5, FGF7 through FGF10, and FGFR1 through FGFR4 (IIIb and IIIc splice variants) in rat metanephroi from E14 to E21. By in situ hybridization, FGF1 mRNA was detected in the nephrogenic zone, ureteric epithelium, and developing nephron elements. FGFR proteins were localized in a distinct pattern that altered with maturation. FGFR1 was widely distributed in developing metanephric epithelia and mesenchyme, but not in developing interstitium. FGFR2 was also widely distributed in nephron epithelia, particularly in proximal convoluted tubules, but was not detected in metanephric mesenchyme, mesenchymal condensates, or developing interstitium. FGFR3 was localized to mesenchymal condensates, nephron elements, and medullary interstitium but not proximal convoluted tubules. FGFR4 was localized mostly to maturing nephron structures and was not detected in nephrogenic mesenchyme, mesenchymal condensates, or developing interstitium.

PRLR: Prolactin Receptor

The interaction between cyclophilin a and the PRLR plays a differential regulatory role in the various signaling pathways leading from the PRLR. Tissue-specific gene expression of prolactin receptor in the acute-phase response induced by lipopolysaccharides. Acute inflammation can elicit a defense reaction known as the acute-phase response (APR) that is crucial for re-establishing homeostasis in the host. The role for prolactin (PRL) as an immunomodulatory factor maintaining homeostasis under conditions of stress has been proposed; however, its function during the APR remains unclear. It has been shown that proinflammatory cytokines characteristic of the APR (TNF-alpha, IL-1 beta, and IFN-gamma) induced the expression of the PRL receptor (PRLR) by pulmonary fibroblasts in vitro. The in vivo expression of PRLR has also been investigated during lipopolysaccharide (LPS)-induced APR in various tissues of the mouse. PRLR mRNA and protein levels were downregulated in hepatic tissues after intraperitoneal LPS injection. A suppressive effect on mRNA expression was also observed in prostate, seminal vesicle, kidney, heart, and lung tissues. These findings suggest a complex tissue-specific regulation of PRLR expression in the context of the APR.

APOM: Apolipoprotein M

Apolipoprotein M (apoM) is a 26-kDa protein that is mainly associated with high-density lipoprotein (HDL) in human plasma, with a small proportion present in triglyceride-rich lipoproteins (TGRLP) and low-density lipoproteins (LDL). It belongs to lipocalin protein superfamily. Human tissue expression array study indicates that apoM is only expressed in liver and in kidney and small amounts are found in fetal liver and kidney. In situ apoM mRNA hybridization demonstrates that apoM is exclusively expressed in the hepatocytes and in the tubule epithelial cells in kidney. Expression of apoM could be regulated by platelet activating factor (PAF), transforming growth factors (TGF), insulin-like growth factor (IGF) and leptin in vivo and/or in vitro.

Peroxisome Proliferative Activated Receptor, Gamma, Coactivator 1, Alpha (PPARGC1A)

The protein encoded by this gene is a transcriptional coactivator that regulates the genes involved in energy metabolism. This protein interacts with PPARgamma, which permits the interaction of this protein with multiple transcription factors. This protein can interact with, and regulate the activities of, cAMP response element binding protein (CREB) and nuclear respiratory factors (NRFs). It provides a direct link between external physiological stimuli and the regulation of mitochondrial biogenesis, and is a major factor that regulates muscle fiber type determination. This protein may be also involved in controlling blood pressure, regulating cellular cholesterol homoeostasis, and the development of obesity.

AKAP12: A Kinase Anchor Protein (Gravin) 12

The A-kinase anchor proteins (AKAPs) are a group of structurally diverse proteins, which have the common function of binding to the regulatory subunit of protein kinase A (PKA) and confining the holoenzyme to discrete locations within the cell. This gene encodes a member of the AKAP family. The encoded protein is expressed in endothelial cells, cultured fibroblasts, and osteosarcoma cells. It associates with protein kinases A and C and phosphatase, and serves as a scaffold protein in signal transduction. This protein and RII PKA colocalize at the cell periphery. This protein is a cell growth-related protein.

Col6A1: Collagen Type VI, Alpha 1

The collagens are a superfamily of proteins that play a role in maintaining the integrity of various tissues. Collagens are extracellular matrix proteins and have a triple-helical domain as their common structural element. Collagen VI is a major structural component of microfibrils. The basic structural unit of collagen VI is a heterotrimer of the alpha1(VI), alpha2(VI), and alpha3(VI) chains. The alpha2(VI) and alpha3(VI) chains are encoded by the COL6A2 and COL6A3 genes, respectively. The protein encoded by this gene is the alpha 1 subunit of type VI collagen (alpha1(VI) chain). Mutations in the genes that code for the collagen VI subunits result in the autosomal dominant disorder, Bethlem myopathy.

PFKFB3: 6-phosphofructo-2-kinase/fructose-2,6-biphosphatase 3

When oxygen becomes limiting, cells shift primarily to a glycolytic mode for generation of energy. A key regulator of glycolytic flux is fructose-2,6-bisphosphate (F-2,6-BP), a potent allosteric regulator of 6-phosphofructo-1-kinase (PFK-1). The levels of F-2,6-BP are maintained by a family of bifunctional enzymes, 6-phosphofructo-2-kinase/fructose-2,6-bisphosphatase (PFKFB or PFK-2), which have both kinase and phosphatase activities. Each member of the enzyme family is characterized by their phosphatase:kinase activity ratio (K:B) and their tissue-specific expression. Previous work demonstrated that one of the PFK-2 isozyme genes, PFKFB-3, was induced by hypoxia through the hypoxia-inducible factor-1 (HIF-1) pathway. The basal and hypoxic expression of three members of this family in different organs of mice was also studied. The findings indicate that all four isozymes (PFKFB-1-4) are responsive to hypoxia in vivo. However, their basal level of expression and hypoxia responsiveness varies in the different organs studied. Particularly, PFKFB-1 is highly expressed in liver, heart and skeletal muscle, with the highest response to hypoxia found in the testis. PFKFB-2 is mainly expressed in the lungs, brain and heart. However, the highest hypoxia responses are found only in liver and testis. PFKFB-3 has a variable low basal level of expression in all organs, except skeletal muscle, where it is highly expressed. Most importantly, its hypoxia responsiveness is the most ample of all three genes, being strongly induced in the lungs, liver, kidney, brain, heart and testis. Further studies showed that PFKFB-1 and PFKFB-2 were highly responsive to hypoxia mimics such as transition metals, iron chelators and inhibitors of HIF hydroxylases, suggesting that the hypoxia responsiveness of these genes is also regulated by HIF proteins. The data demonstrate that PFK-2 genes are responsive to hypoxia in vivo, indicating a physiological role in the adaptation of the organism to environmental or localized hypoxia/ischemia.

TGF-Beta1: Transforming Growth Factor-Beta1

Transforming growth factor-beta1 (TGF-beta1) a multifunctional growth cytokine, has been implicated in the pathogenesis of chronic allograft nephropathy. In chronic renal graft rejection urine secretion of TGF-beta1 was increased; urine secretion of TGF-beta1 was associated with arterial hypertension, degree of interstitial tissue fibrosis, and progression of graft insufficiency; the negative correlation between HDL level and urine secretion of TGF-beta1 (both in patients with chronic rejection and in recipients with a stable graft function) suggests the influence of dyslipidemia on the secretion of this growth factor (10850587).

IGF2: Insulin-Like Growth Factor 2 (Somatomedin A)

Insulin-like growth factor 2 (IGF2) gene variant is associated with overfeeding-induced metabolic changes. Loss of genomic imprinting of IGF-2 is strongly associated with cellular proliferation in normal hematopoietic cells. Fibroblast proliferation, differentiation into myofibroblasts, and increased collagen synthesis are regulated via a CTGF-dependent pathway in concert with either EGF or IGF-2.

ALB: Albumin

Albumin affects glucose metabolism by impairing insulin-induced insulin receptor substrate (IRS) signaling through a protein kinase C alpha-mediated mechanism. Albumin acts as a specific molecular adsorbent. Remove of albumin-bound molecules, such as bilirubin, bile acids, aromatic amino acids and copper is clinically accompanied with an improvement of liver, cardiovascular and renal functions and hepatic encephalopathy.

MAPT: Microtubule-Associated Protein Tau

MAP2C and TAU stabilize microtubules by binding along individual protofilaments, possibly by bridging the tubulin interfaces. The interactions between alpha-synuclein and tau can promote their fibrillization and drive the formation of pathological inclusions in human neurodegenerative diseases.

MAL2: Mal, T-cell Differentiation Protein 2

Data show that MAL2 is essential for transcytosis in HEPG2 cells. MAL2 protein mRNA species were detected in the thyroid and immunohistochemical analysis of thyroid follicles indicated that MAL2 distributed to the apical membrane.

LOC285148 (ADAM 17)

ADAM9, ADAM10, and ADAM17, are members of the disintegrin and metalloprotease family, catalyze alpha-secretory cleavage and therefore act as alpha-secretases in A172 cells. ADAM-17 is a potent activator of *vibrio cholerae* procytolysin. ADAM-17/TACE and TIMP-3 may also play an important role in the pathogenesis of prostate cancer.

FLNC: Filamin C, Gamma (Actin Binding Protein 280)

may be substrate for Calpain 3, regulating protein-protein interactions with sarcoglycans. Accumulation is a strong but nonspecific immunohistochemical marker of core formation in muscle myopathies.

PAWR: PRKC, apoptosis, WT1, regulator

PAR-4 increases apoptosis by upregulating the CD95 receptor on the cell surface and, with concomitant decrease of the Flice-like inhibitory protein (FLIP), by promoting cleavage of the initiator caspases-8 and -10. PAR-4 is directly involved in regulating choline uptake by interacting with CHT1 and by reducing its incorporation on the cell surface.

SCA7: Ataxin 7

Identification of a novel ATAXIN-7 protein enriched in the central nervous system suggests that expression of multiple polyglutamine-containing proteins may play a role in the neurodegeneration patterns characteristic of SCA7.

ACMSD: Alpha-Amino-Beta-Carboxymuconate-Epsilon-Semialdehyde Decarboxylase

Marked increases in metabolites of the L-tryptophan-kynurenine pathway, L-kynurenine and quinolinic acid (Quin), were observed in serum and cerebrospinal fluid (CSF) of both the rat and human with renal insufficiency. The mechanisms responsible for their accumulation after renal insufficiency were investigated. In patients with chronic renal insufficiency, elevated levels of serum L-kynurenine and Quin were reduced by hemodialysis. In renal-insufficient rats, Quin and L-kynurenine levels in serum, brain, and CSF were also increased parallel to the severity of renal insufficiency. Urinary excretion of Quin (3.5-fold) and L-kynurenine (2.8-fold) was also increased. Liver L-tryptophan 2,3-dioxygenase activity (TDO), a rate-limiting enzyme of the kynurenine pathway, was increased in proportion to blood urea nitrogen and creatinine levels. Kynurenine 3-hydroxylase and quinolinic acid phosphoribosyltransferase were unchanged, but the activities of kynureninase, 3-hydroxyanthranilate dioxygenase, and aminocarboxymuconate-semialdehyde decarboxylase (ACMSDase) were significantly decreased. Systemic administrations of pyrazinamide (ACMSDase inhibitor) increased serum Quin concentrations in control rats, demonstrating that changes in body ACMSDase activities in response to renal insufficiency are important factors for the determination of serum Quin concentrations. Increased serum L-kynurenine concentrations are mainly due to the increased TDO and decreased kynureninase activities in the liver and increased serum Quin concentrations are due to the decreased ACMSDase activities in the body after renal insufficiency. The accumulation of CSF L-kynurenine is caused by the entry of increased serum L-kynurenine, and the accumulation of CSF Quin is secondary to Quin from plasma and/or Quin precursor into the brain.

ACOX2

During allograft rejection, cytokines and lipid mediators contribute to cell injury and organ failure. Peroxisomes play a crucial role in lipid metabolism, including the degradation of lipid mediators by peroxisomal beta-oxidation. Alterations of hepatic peroxisomes after allogeneic rat liver transplantation were investigated. MHC-incompatible Dark Agouti (RT1a) donor rats and Lewis (RT1(1)) recipient rats were used for allogeneic transplantation. For immunosuppression, a group of these animals received cyclosporine (CsA) intraperitoneally (1 mg/kg body weight per day). Lewis rats were used for isogeneic transplant combination. Ten days after transplantation, livers were investigated using morphometrical methods for determination of peroxisomal diameter and volume density. The activities of peroxisomal catalase (CAT) and acyl-coenzyme A oxidase (AOX) were determined, and the corresponding proteins were evaluated by quantitative immunocytochemistry and immunoblotting. The expressions of mRNAs encoding CAT and AOX were investigated by Northern blotting.

The volume density and diameter of peroxisomes were significantly decreased in allogeneic transplanted livers but were unchanged in CsA-treated animals. Both the activities of CAT and AOX and their protein levels were significantly reduced in liver allografts. Moreover, the corresponding mRNA levels of CAT and AOX were decreased significantly in liver allografts, whereas CsA treatment led to an increase of those mRNAs. Isogeneic transplanted livers showed only a slight reduction of the corresponding enzyme values. CONCLUSIONS: Peroxisomes are severely affected both morphologically and functionally after allogeneic liver transplantation. These results suggest that impairment of peroxisomal lipid beta-oxidation could contribute to the pathogenesis of the rejection process by decreased catabolism of lipid mediators involved in the regulation of the inflammatory response. CsA, in addition to its immunosuppressive effects, may contribute to allograft survival by maintenance of those important peroxisomal functions. (Steinmetz et al., Transplantation. 1998 Jul. 27; 66(2):186-94.)

ADAM17

Chronic renal allograft rejection is characterized by alterations in the extracellular matrix compartment and in the proliferation of various cell types. These features are controlled, in part by the metzincin superfamily of metallo-endopeptidases, including matrix metalloproteinases (MMPs), a disintegrin and metalloproteinase (ADAM) and meprin. Therefore, we investigated the regulation of metzincins in the established Fisher to Lewis rat kidney transplant model. Studies were performed using frozen homogenates and paraffin sections of rat kidneys at day 0 (healthy controls) and during periods of chronic rejection at day +60 and day +100 following transplantation. The messenger RNA (mRNA) expression was examined by Affymetrix Rat Expression Array 230A GeneChip and by real-time Taqman polymerase chain reaction analyses. Protein expression was studied by zymography, Western blot analyses, and immunohistology. mRNA levels of MMPs (MMP-2/-11/-12/-14), of their inhibitors (tissue inhibitors of metalloproteinase (TIMP)-1/-2), ADAM-17 and transforming growth factor (TGF)-beta1 significantly increased during chronic renal allograft rejection. MMP-2 activity and immunohistological staining were augmented accordingly. The most important mRNA elevation was observed in the case of MMP-12. As expected, Western blot analyses also demonstrated increased production of MMP-12, MMP-14, and TIMP-2 (in the latter two cases as individual proteins and as complexes). In contrast, mRNA levels of MMP-9/-24 and meprin alpha/beta had decreased. Accordingly, MMP-9 protein levels and meprin alpha/beta synthesis and activity were downregulated significantly. Members of metzincin families (MMP, ADAM, and meprin) and of TIMPs are differentially regulated in chronic renal allograft rejection. Thus, an altered pattern of metzincins may represent novel diagnostic markers and possibly may provide novel targets for future therapeutic interventions. (Berthier et al., Kidney Int. 2006 February; 69(2):358-68).

AGXT2

Alanine-glyoxylate aminotransferase (AGT) 2 is a pyridoxal 5'-phosphate dependent, mitochondrial enzyme which, in the rat, is expressed at a high level in the kidney. (Lee I S et al., Nephron. 1999; 83(2):184-5).

ALAD

Compromised renal function after renal allograft transplantation often results in anemia in the recipient. Molecular mechanisms leading to anemia during acute rejection are not fully understood; inadequate erythropoietin production and iron deficiency have been reported to be the main contributors. To increase our understanding of the molecular events underlying anemia in acute rejection, the gene expression profiles of peripheral blood lymphocytes (PBL) from four pediatric renal allograft recipients with acute rejection and concurrent anemia were examined, using DNA microarrays containing 9000 human cDNA clones (representing 7469 unique genes). In these anemic rejecting patients, an 'erythropoiesis cluster' of 11 down-regulated genes was identified, involved in hemoglobin transcription and synthesis, iron and folate binding and transport. Additionally, some alloimmune response genes were simultaneously down-regulated. An independent data set of 36 PBL samples, some with acute rejection and some with concurrence of acute rejection and anemia, were analyzed to support a possible association between acute rejection and anemia. In conclusion, analysis using DNA microarrays has identified a cluster of genes related to hemoglobin synthesis and/or erythropoeisis that was altered in kidneys with renal allograft rejection compared with normal kidneys. The possible relationship between alterations in the expression of this cluster, reduced renal function, the alloimmune process itself, and other influences on the renal transplant awaits further analysis. (Chua et al., Am J. Transplant. 2003 January; 3(1): 17-22).

ALAS2

Iron-regulatory proteins (IRPs) 1 and 2 posttranscriptionally regulate expression of transferrin receptor (TfR), ferritin, and other iron metabolism proteins. Ablation of IRP2 results in iron-limited erythropoiesis. TfR expression in erythroid precursors of IRP2−/− mice is reduced, and bone marrow iron stores are absent, even though transferrin saturation levels are normal. Marked overexpression of 5-aminolevulinic acid synthase 2 (ALAS2) results from loss of IRP-dependent translational repression, and markedly increased levels of free protoporphyrin IX and zinc protoporphyrin are generated in IRP2−/− erythroid cells. IRP2−/− mice represent a new paradigm of genetic microcytic anemia. IRP2 mutations or deletions may be a cause of refractory microcytic anemia and bone marrow iron depletion in patients with normal transferrin saturations, elevated serum ferritins, elevated red cell protoporphyrin IX levels, and adult-onset neurodegeneration (Cooperman S S et al. Blood. 2005 Aug. 1; 106(3):1084-91. Epub 2005 Apr. 14.)

ALDH7A1

Betaine plays an important role in the osmoregulation of various renal cells. In the kidney betaine synthesis seems to be highest in the cortex, whereas osmotically regulated accumulation seems to play a crucial role in the inner medulla. The alteration of betaine synthesis is presumably caused by osmotic regulation of the betaine aldehyde dehydrogenase. Activity of this enzyme was significantly higher under hyperosmotic conditions compared to isoosmotic control conditions. These results demonstrate that during long-term adaptation, betaine synthesis in TALH cells of the outer medulla of rabbit kidney can be regulated by extracellular osmolarity. (Furuyama K et al., Blood. 2003 Jun. 1; 101(11):4623-4. Epub 2003 Jan. 16).

BHMT2

Glycine betaine supplementation lowers homocysteine levels in homocystinuria and in chronic renal failure patients through methylation catalysed by betaine-homocysteine methyltransferase (BHMT). Glycine betaine, proline betaine, trigonelline, dimethylsulfoniopropionate (DMSP) or dimethylthetin (1.5 mmoles) was subcutaneously administered to rats fed a low betaine diet. The effect of each betaine on total plasma homocysteine and urinary and plasma betaine concentrations was monitored. The effect of glycine betaine, DMSP and dimethylthetin on circulating homocysteine concentrations was mediated by BHMT in vivo. Circulating glycine betaine concentrations increased following DMSP and dimethylthetin treatment. Urinary excretion of glycine betaine increased following treatment with all betaines, suggesting that the resorption of glycine betaine in the kidney was inhibited. The study shows that glycine betaine analogues have multiple effects on homocysteine metabolism (Slow S. et al., Int J Biochem Cell Biol. 2004 May; 36(5): 870-80.0

CCL28

The chemokine CCL28 is constitutively expressed by epithelial cells at several mucosal sites and is thought to function as a homeostatic chemoattractant of subpopulations of T cells and IgA B cells and to mediate antimicrobial activity. In vivo, CCL28 was markedly increased in the epithelium of pathologically inflamed compared with normal human colon. Human colon and small intestinal xenografts were used to model human intestinal epithelium in vivo. Consistent with its upregulated expression by proinflammatory stimuli, CCL28 mRNA expression was attenuated by pharmacological inhibitors of NF-kappaB activation. These findings indicate that CCL28 functions as an "inflammatory" chemokine in human colon epithelium and suggest the notion that CCL28 may act to counterregulate colonic inflammation (Ogawa et al., Am J Physiol Gastrointest Liver Physiol. 2004 November; 287(5):G1062-9. Epub 2004 Jul. 8.)

DCXR

Carbonyl compounds in the blood stream tend to accumulate in the kidney of diabetic or end stage renal failure subjects. Previously the cDNA encoding dicarbonyl/L-xylulose reductase (DCXR) was isolated from a mouse kidney cDNA library. The functional role of DCXR in the kidney was examined in Tg mice. With a six-fold increase in the DCXR protein expression levels in the kidney, the homozygous Tg mice did not show any notable histological abnormalities. While the elevated DCXR expression was observed throughout the body, its renal distribution was similar to that of the endogenous DCXR protein, namely, the major expression site was the collecting tubules, along with moderate expression in other tubules and Bowman's capsule, but it was absent from the interstitial area and glomeruli. The Tg mice were crossed with KK-A(y) diabetic model mice to examine the role of DCXR in the progression of diabetic nephropathy. The resulting progeny, Tg/A(y), showed lighter body weight, lower levels of blood glucose, water uptake and creatinine clearance compared to their +/A(y) littermates. Although remarkable pathological differences were not observed at the microscopic level and in the renal accumulation of carboxymethyl lysine, the data imply that DCXR might function in the metabolism of glucose or carbonyl compounds, and play a protective role in a kidney which is under hyperglycemic pressure. The DCXR Tg mice and the Tg×KK-A(y) hybrid mice, therefore, serve as specific models for carbonyl metabolism in the kidney with diabetic background. (Sudo et al., Transgenic Exp Anim. 2005 October; 54(5):385-94.)

EHF

The ets family is a large multigene family of transcription factors that share a conserved DNA-binding "ETS" domain and include several oncoproteins that induce tumorigenesis when overexpressed. The cDNA was cloned, sequenced and charactereized from mouse pituitary somatotroph tumors, to show a novel ets family gene, "Ehf" ("ets homologous factor"). The putative 300 amino acid Ehf protein is a highly divergent ets family member, but is most related to the recently identified oncoprotein ESX (36% overall and 84% ETS domain amino acid identity). Thus, Ehf and ESX comprise a new ets subfamily. Ehf is a single-copy gene, but produces four distinct mRNA transcripts. Ehf transcripts are abundant in mouse kidney and lung, less so in muscle and liver, and not detected in brain, spleen or testes. Because of its presence in somatotroph tumors and its relationship to ESX, Ehf may represent a new oncoprotein. (Bochert M A et al., Biochem Biophys Res Commun. 1998 May 8; 246(1):176-81).

Other preferred genes that are relevant include, but are not limited to, EPHX2 (Imig J D et al., Hypertension. 2005 October; 46(4):975-81. Epub 2005 Sep. 12), FKBP11 (Han I S et al., J Korean Med. Sci. 2002 February; 17(1):41-8); Sheppard K E, J. Neuroendocrinol. 1995 November; 7(11):833-40), FMO4 (Zhang J et al., Drug Metab Dispos. 2006 January; 34(1):19-26. Epub 2005 Sep. 23; Krause R J et al., J Pharmacol Exp Ther. 2003 January; 304(1): 185-91), FNBP2 (Chan D C et al., EMBO J. 1996 Mar. 1; 15(5):1045-54), FUBP1 (Scholz H et al., J Biol. Chem. 1997 Dec. 26; 272(52):32836-46), FUT3 (Xia L et al., Blood. 2004 Nov. 15; 104(10):3091-6. Epub 2004 Jul. 27; Yan J L et al., Acta Pharmacol Sin. 2003 September; 24(9):878-84; Rhim A D et al., Glycoconj J. 2001 September; 18(9):649-59; Lacha J et al., J Leukoc Biol. 2002 February; 71(2):311-8; Poland D C et al., Glycoconj J. 2001 March; 18(3):261-8.; Artrip J H et al., Erratum in: J Biol Chem 1999 May 21; 274(21):15292; Cooper D K, Xenotransplantation. 1998 February; 5(1):6-17; Cowan P J et al., Transplantation. 1998 Jun. 27; 65(12): 1599-604; Chen C G et al., Transplantation. 1998 Mar. 27; 65(6):832-7; Osman N et al., Proc Natl Acad Sci USA. 1997 Dec. 23; 94(26):14677-82), GAS5 (Bek M F et al., Am J. Pathol. 2006 January; 168(1): 20-32; Lake A C et al., Cell Commun Signal. 2003 Nov. 24; 1(1):5), HAGH (Mulley J C et al., Hum Genet. 1986 December; 74(4):423-4), HCCR1 (Chung Y J et al., Histol Histopathol. 2005 July; 20(3):999-1003); K o J et al., Oncogene. 2003 Jul. 24; 22(30):4679-89), HPN: Hepsin (Li Y et al., Biochim Biophys Acta. 2005 Jan. 11; 1681(2-3):157-65. Epub 2004 Dec. 15; Roemer A et al., J. Urol. 2004 December; 172(6 Pt 1):2162-6), INSL3 (Fu P et al., Ann N Y Acad Sci. 2005 May; 1041:516-9), IQGAP1 (Lehtonen S et al., Proc Natl Acad Sci USA. 2005 Jul. 12; 102(28):9814-9. Epub 2005; Jia Z et al., J Biol. Chem. 2005 Aug. 26; 280(34): 30564-73. Epub 2005 Jun. 28), KCNJ15 (Derst C et al., J Biol. Chem. 1998 Sep. 11; 273(37):23884-91; Shuck M E et al., J Biol. Chem. 1997 Jan. 3; 272(1):586-93), KCNN2 (Kusaka M et al., Transplant Proc. 2005 January-February; 37(1):364-6), KIF13B (Venkateswarlu K et al., J Cell Sci. 2005 Jun. 1; 118(Pt 11):2471-84), LRP2 (de Jong M et al., J Nucl Med. 2005 October; 46(10):1696-700), Oleinikov A V et al., J. Pathol. 2000 October; 192(2):251-6), PDZK I (Miyazaki H et al., J Am Soc Nephrol. 2005 December; 16(12):3498-506. Epub 2005 Oct. 19), PLD1 (Zhao Y et al., Biochem Biophys Res Commun. 2000 Nov. 11; 278(1):140-3; Slaaby R et al., Biochem J. 2000 Nov. 1; 351 Pt 3:613-9), PNPN (Okuda T et al., Biochem Biophys Res Commun. 2004 Jan. 16; 313(3):647-53, RTKN (Liu C A et al., J Biomed Sci. 2004 September-October; 11(5):661-70), SLC34A I (Baum M et al., Kidney Int. 2005 September; 68(3):1148-53; Nashiki K et al., Kidney Int. 2005 September; 68(3):1137-47), SLC7A9 (Yuen Y P et al., Kidney Int. 2006 January; 69(1):123-8), SLPI (He Z et al., J Mol. Med. 2003 October; 81(10):600-12. Epub 2003 Aug. 19), THEM2 (Lucas et al., Oncogene. 2005 Sep. 22; 24(42):6418-31).

DISCUSSION

Gene expression profiling of serial renal allograft protocol biopsies was performed with the goal to identify genomic biomarkers for prediction/early diagnosis of CAN. The biomarkers are useful as molecular tools to diagnose CAN before CAN is manifest by histological parameters.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled.

We claim:

1. A method for assessing the onset or progression of chronic or sclerosing allograft nephropathy of a transplanted kidney in a post-transplantation subject, said method comprising, comparing a post-transplantation magnitude of gene expression for each gene identified in Table 2 in a post-transplantation sample from the post-transplantation subject with a control magnitude of gene expression for each gene identified in Table 2 in a control sample from a non-transplanted subject, wherein a difference in all post-transplantation magnitudes of gene expression by a factor of at least about 1.1 compared to all corresponding control magnitudes of gene expression indicates the onset or progression of chronic or sclerosing allograft nephropathy of the transplanted kidney in the post-transplantation subject.

2. The method according to claim 1, further comprising detecting the magnitude of gene expression in the post-transplantation sample prior to said step of comparing.

3. The method of claim 1, wherein the chronic or sclerosing allograft nephropathy is at a stem selected from the group consisting of: grade I, grade II, and grade III.

4. The method of claim 1, wherein the post-transplantation sample comprises cells obtained from the post-transplantation subject.

5. The method of claim 1, wherein the post-transplantation sample is selected from the group consisting of a biopsy sample; a blood sample; a serum sample; and a urine sample.

6. The method of claim 2, wherein the post-transplantation magnitude of gene expression is detected by a technique selected from the group consisting of Northern blot analysis, reverse transcription PCR and real time quantitative PCR.

7. The method of claim 1, wherein the post-transplantation magnitude of gene expression differs from the control magnitude of gene expression by a factor of at least about 1.5.

8. A method of monitoring chronic or sclerosing allograft nephropathy of a transplanted kidney in a post-transplantation subject, said method comprising, comparing a post-transplantation magnitude of gene expression for each gene identified in Table 2 in a post-transplantation sample obtained from the post-transplantation subject with a control magnitude of gene expression for each gene identified in Table 2 in a control sample obtained from a transplanted subject known not to develop rejection, wherein a difference in all post-transplantation magnitudes of gene expression by a factor of at least about 1.1 compared to the all corresponding control magnitude magnitudes of gene expression provides an indication that the subject is rejecting the transplanted kidney, thereby monitoring rejection of the transplanted kidney in the post-translation subject.

9. The method according to claim 8, further comprising detecting the magnitude of gene expression in the post-transplantation sample prior to said step of comparing.

10. The method of claim 8, wherein the chronic or sclerosing allograft nephropathy is at a stage selected from the group consisting of: grade I, grade II, and grade III.

11. The method of claim 8, wherein the post-transplantation sample comprises cells obtained from the post-transplantation subject.

12. The method of claim 8, wherein the post-transplantation sample is selected from the group consisting of a biopsy sample; a blood sample; a serum sample; and a urine sample.

13. The method of claim 9, wherein the post-transplantation magnitude of gene expression is detected by a technique selected from the group consisting of Northern blot analysis, reverse transcription PCR and real time quantitative PCR.

14. The method of claim 8, wherein the post-transplantation magnitude of gene expression differs from the control magnitude of gene expression in by a factor of at least about 1.5.

* * * * *